(12) United States Patent
Anderson et al.

(10) Patent No.: US 6,843,134 B2
(45) Date of Patent: Jan. 18, 2005

(54) RING ROLLING SIMULATION PRESS

(75) Inventors: Barry Jay Anderson, Cincinnati, OH (US); Michael Joseph Lamping, Cincinnati, OH (US); Eugene Paul Daut, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 104 days.

(21) Appl. No.: 10/377,070

(22) Filed: Feb. 28, 2003

(65) Prior Publication Data

US 2004/0099158 A1 May 27, 2004

Related U.S. Application Data

(63) Continuation-in-part of application No. 10/377,070, filed on Feb. 28, 2003.
(60) Provisional application No. 60/429,802, filed on Nov. 27, 2002.

(51) Int. Cl.[7] ................................................. G01L 1/00
(52) U.S. Cl. ........................................... 73/763; 100/48
(58) Field of Search .......................... 73/763, 769, 818, 73/824, 866; 100/48

(56) References Cited

U.S. PATENT DOCUMENTS

| | | | | |
|---|---|---|---|---|
| 4,074,624 A | * | 2/1978 | Biornstad et al. | 100/35 |
| 4,420,958 A | * | 12/1983 | Schulz et al. | 72/21.1 |
| 4,812,722 A | | 3/1989 | Corrothers | |
| 5,167,799 A | * | 12/1992 | Severin et al. | 210/85 |
| 5,188,456 A | | 2/1993 | Burke et al. | |
| 5,351,553 A | | 10/1994 | Lepie et al. | |
| 5,562,027 A | * | 10/1996 | Moore | 100/35 |
| 5,575,078 A | | 11/1996 | Moulton, III | |
| 5,767,402 A | | 6/1998 | Sandlass et al. | |
| 5,974,853 A | * | 11/1999 | Strong et al. | 72/430 |
| 6,370,962 B1 | | 4/2002 | Sullivan et al. | |
| 6,410,820 B1 | | 6/2002 | McFall et al. | |
| 6,500,377 B1 | | 12/2002 | Schneider et al. | |

FOREIGN PATENT DOCUMENTS

| | | |
|---|---|---|
| EP | 1 043 579 A1 | 10/2000 |
| WO | WO 99/56685 A1 | 11/1999 |

* cited by examiner

Primary Examiner—Charles D. Garber
(74) Attorney, Agent, or Firm—Jack L. Oney, Jr.; Jay A. Krebs; Ken K. Patel

(57) ABSTRACT

A simulation press is provided comprising a fixed main body; a carriage associated with the main body for movement relative to the main body; a first plate coupled to the fixed main body and being adapted to engage a workpiece; and a second plate coupled to the carriage for movement with the carriage. The second plate is also adapted to engage the workpiece. One or more motor apparatus are coupled to the fixed main body and the carriage for effecting movement of the carriage relative to the main body. A drive controller is coupled to the motor apparatus for controlling the operation of the motor apparatus in response to feedback from one or more feedback sensors so as to cause the second plate to move relative to the first plate such that the first and second plates engage the workpiece and simulate a ring rolling operation on the workpiece.

20 Claims, 21 Drawing Sheets

US 6,843,134 B2

RING ROLLING SIMULATION PRESS

CROSS-REFERENCE TO RELATED APPLICATION

This application is a continuation-in-part of and claims priority to application U.S. Ser. No. 10/377,070, entitled 'RING ROLLING SIMULATION PRESS, filed on Feb. 28, 2003, which application is incorporated by reference herein and, further, which application claims the benefit of U.S. Provisional Application No. 60/429,802, filed Nov. 27, 2002, and entitled RING ROLLING SIMULATION PRESS.

BACKGROUND OF THE INVENTION

It is known in the art to use a press to simulate a low strain activation operation such as the one discussed in published international application WO 99/56685. The press comprised a stationary first plate having first teeth, a second plate having second teeth, a movable ram to which the second plate was coupled, a rotary servo motor coupled to the ram, and a controller for controlling the operation of the rotary servo motor such that the second plate was moved toward the first plate so that a workpiece was engaged by the teeth of the first and second plates. The press did not include sensors of any sort for providing feedback information, such as position or force information concerning the ram, the plates or the motor, to the controller. Nor was the press used to simulate a ring rolling operation.

Accordingly, there is a need for a press for simulating a ring rolling operation.

BRIEF SUMMARY OF THE INVENTION

A simulation press is provided comprising a fixed main body; a carriage associated with the main body for movement relative to the main body; a first plate coupled to the fixed main body and being adapted to engage a workpiece; and a second plate coupled to the carriage for movement with the carriage. The second plate is also adapted to engage the workpiece. One or more motor apparatus are coupled to the fixed main body and the carriage for effecting movement of the carriage relative to the main body. A drive controller is coupled to the motor apparatus for controlling the operation of the motor apparatus in response to feedback from one or more feedback sensors so as to cause the second plate to move relative to the first plate such that the first and second plates engage the workpiece and simulate a ring rolling operation on the workpiece.

DETAILED DESCRIPTION OF THE INVENTION

Figure 1:
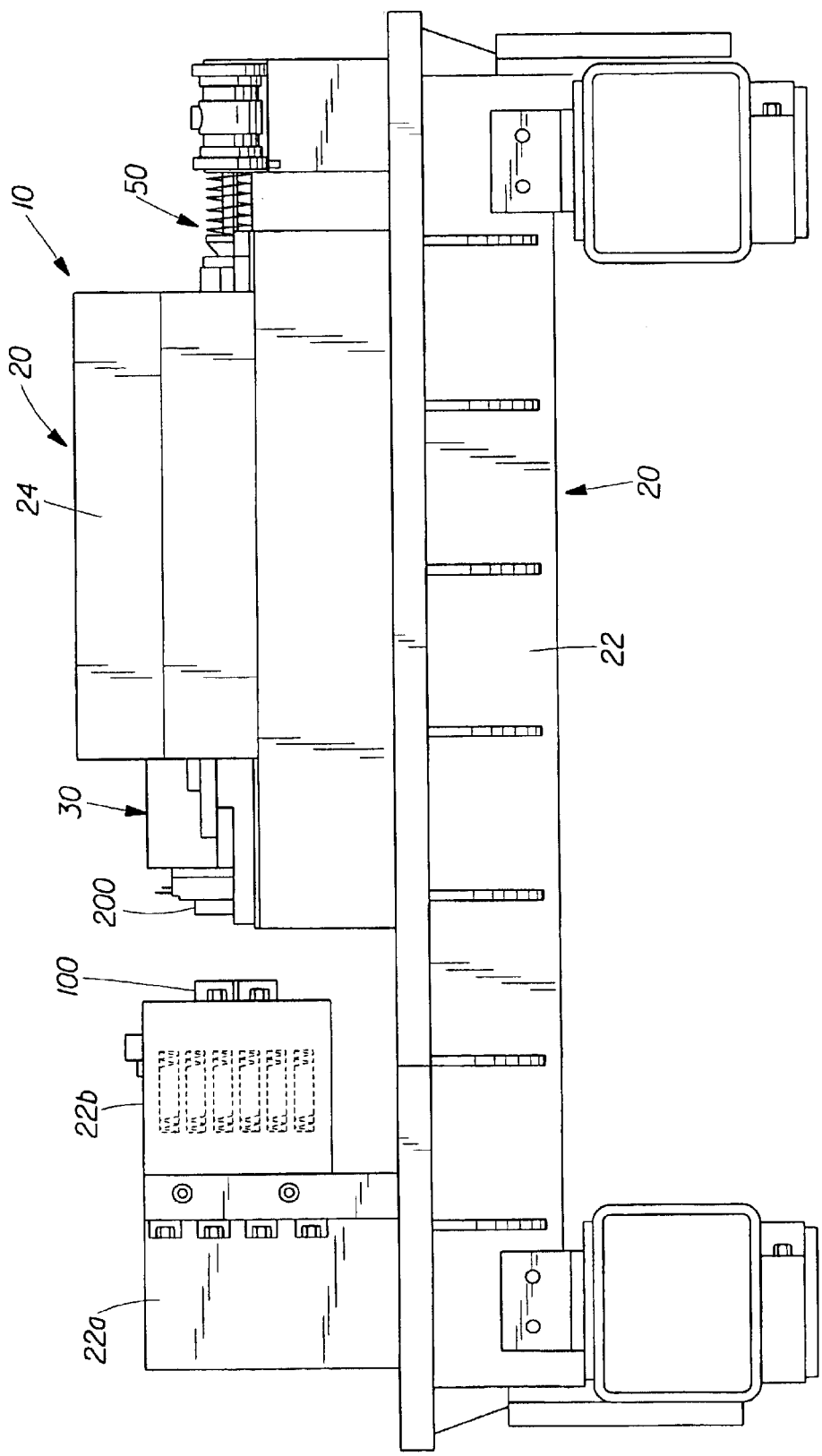
FIG. 1 is a side view of an apparatus of the present invention which functions to replicate work performed by a pair of ring rolling rolls on a web material.
Figure 8:
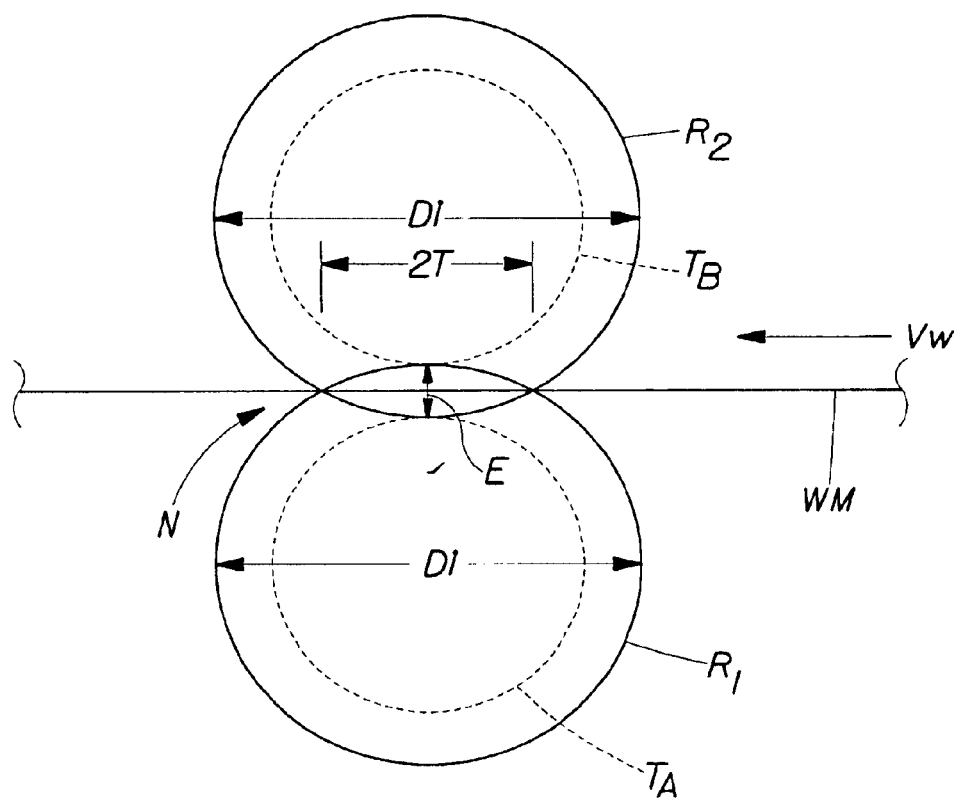
FIG. 8 is a schematic illustration of first and second teeth on first and second rolls engaging during a ring rolling operation.
Figure 8A:
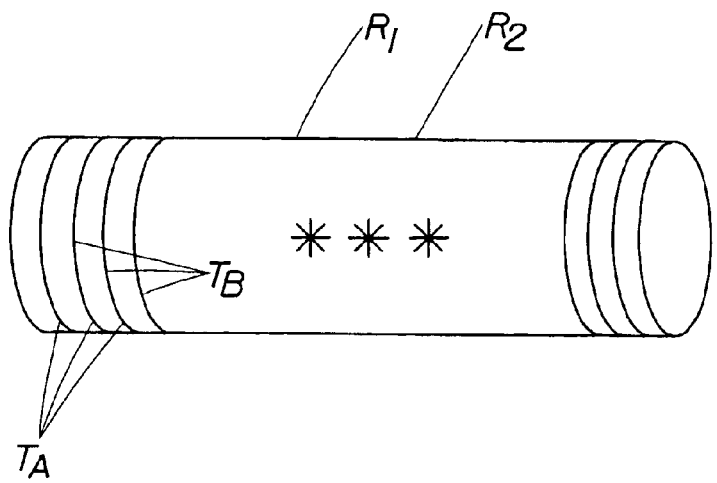
FIG. 8A is a schematic side view of a ring-rolling roll.
Figure 9:
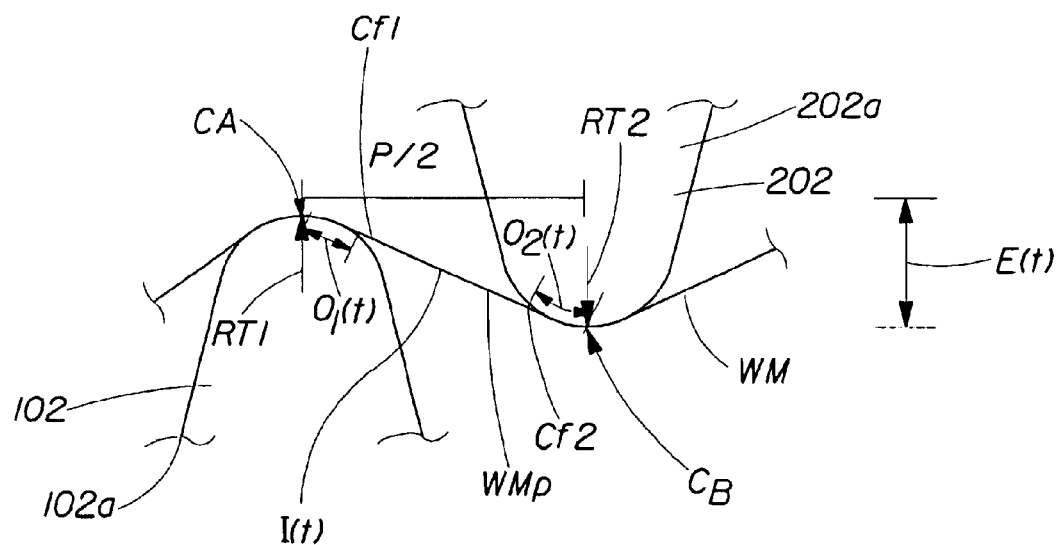
FIG. 9 is a schematic illustration of a first tooth and a second tooth on the first and second plates in engagement with a web material.

An apparatus 10 constructed in accordance with the present invention is illustrated in FIG. 1 and functions to replicate work performed by a pair of ring rolling rolls on a web material as the web material passes through a nip defined by the rolls, wherein the rolls typically have engaging teeth. The apparatus 10 comprises a generally stationary, substantially planar first plate 100 provided with first teeth 102, see FIGS. 1, 5, 12A and 12B, and a linearly movable, substantially planar second plate 200 having second teeth 202, see FIGS. 1, 2A, 12A and 12B. Ring rolling processes comprising rotating first and second rolls, wherein first teeth $T_A$ on the first roll $R_1$ engage with second teeth $T_B$ on the second roll $R_2$, see FIGS. 8, 8A and 9, are known in the art for stretching web materials WM, such as films, webs comprising non-woven fibers, and laminates of films, non-woven webs or like materials, or for modifying the visual appearance of such web materials for aesthetic purposes. The first and second teeth $T_A$ and $T_B$ may be circumferential or substantially parallel to the axes of the rolls $R_1$ and $R_2$. The apparatus 10 of the present invention allows engineers/technicians to quickly and relatively inexpensively test web materials to determine the effects of a ring rolling process on a given web material without actually providing first and second ring rolling rolls, and running web material through a nip defined by the first and second rolls.

Figure 2A:
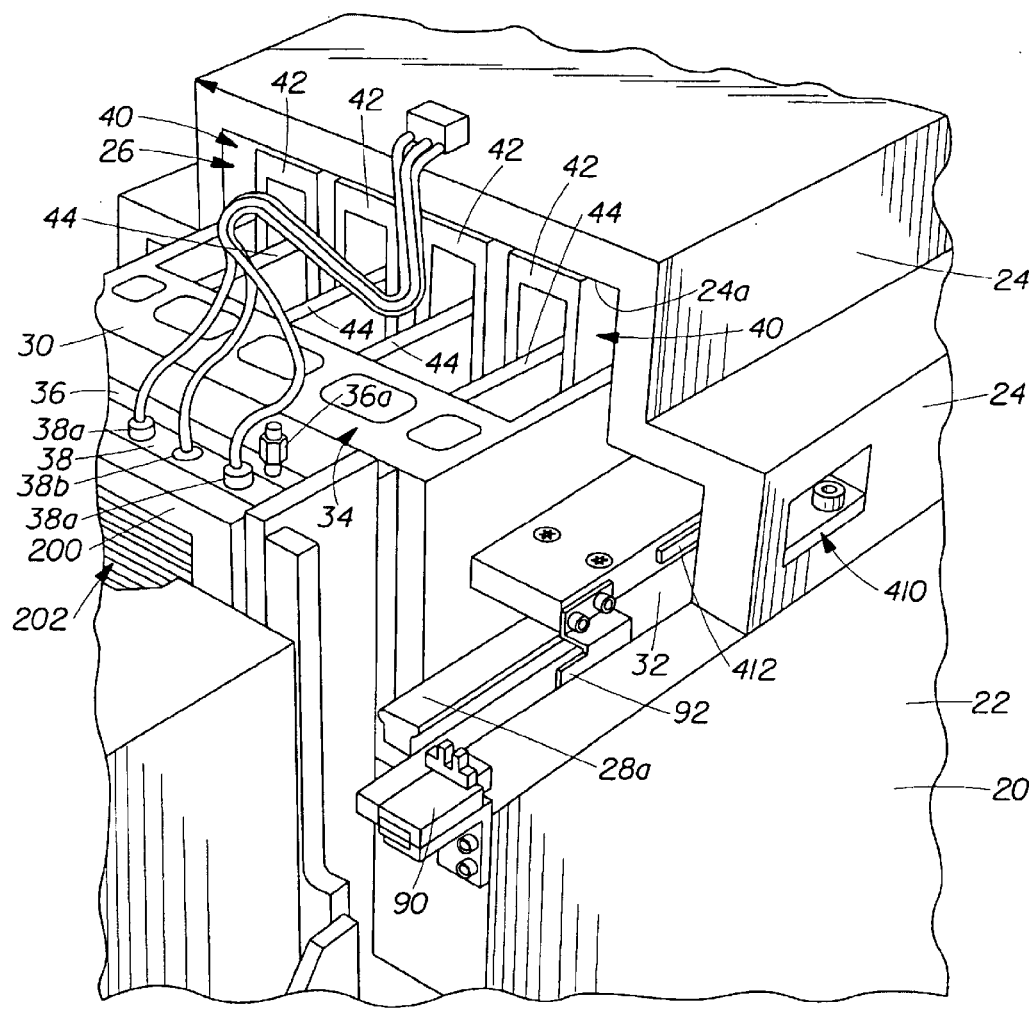
FIG. 2A is a perspective view illustrating a reciprocating carriage provided with a second plate, wherein the carriage is positioned within a cavity defined by the upper and lower portions of a main body of the apparatus.
Figure 2B:
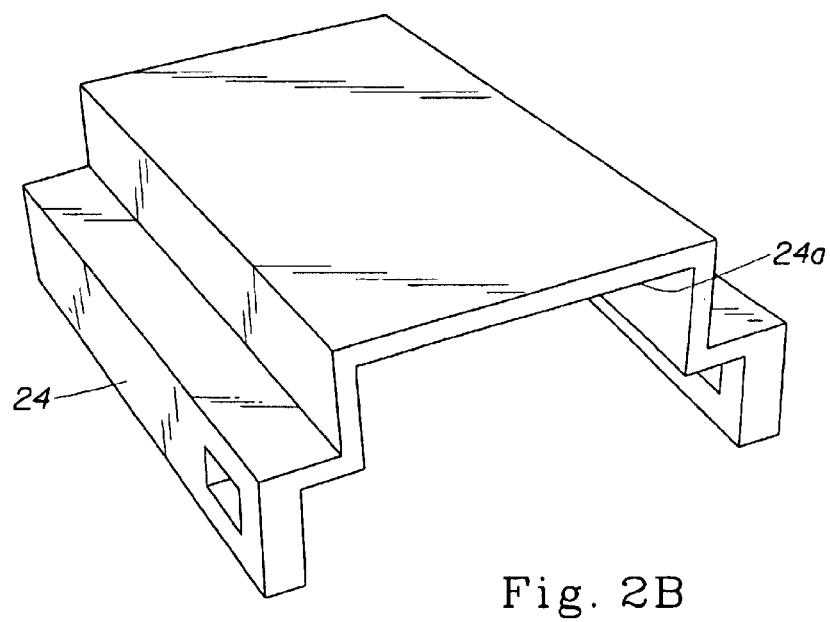
FIG. 2B is a perspective view of the upper portion of the apparatus main body.
Figure 2C:
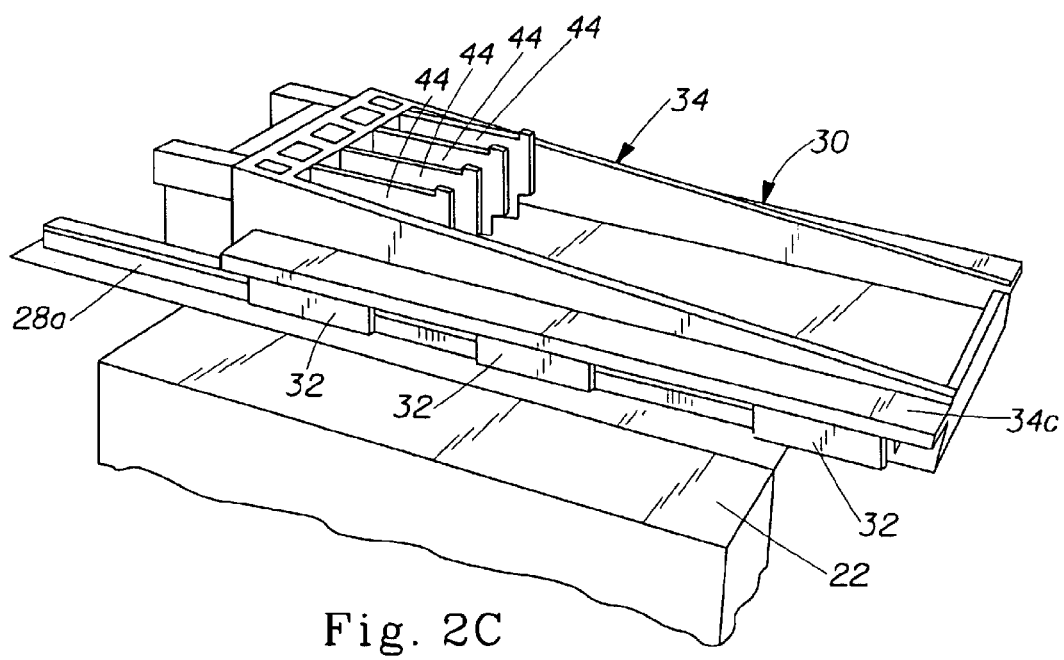
FIG. 2C is a perspective side view of the carriage mounted to the main body lower portion and wherein the main body upper portion and linear servo motors have been removed.
Figure 2D:
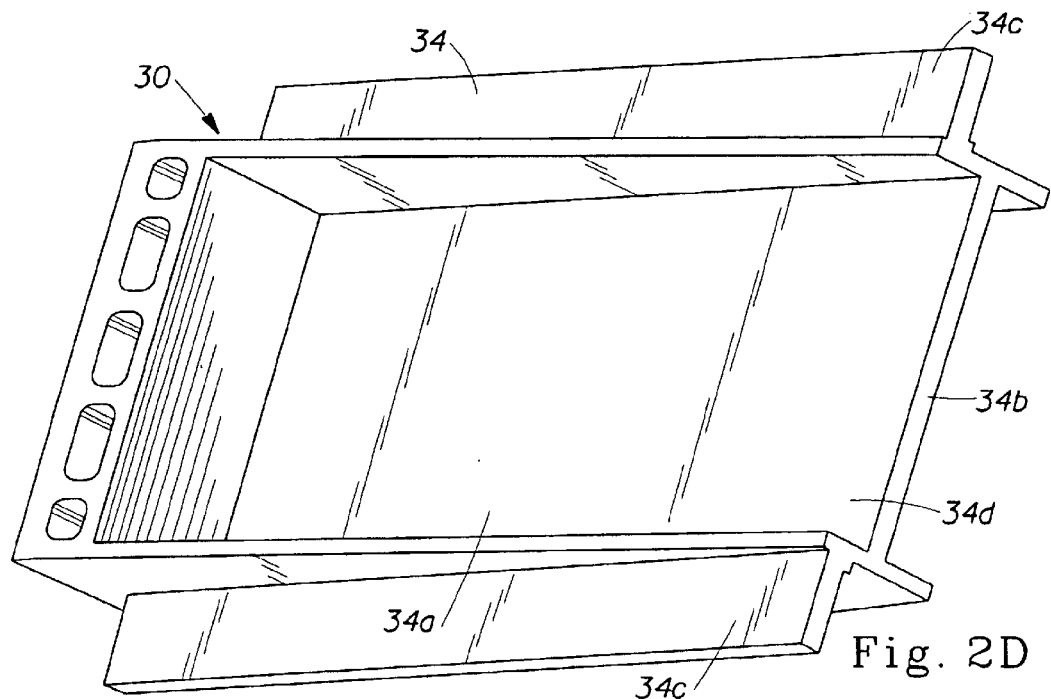
FIG. 2D is perspective view of the carriage main body.
Figure 2E:
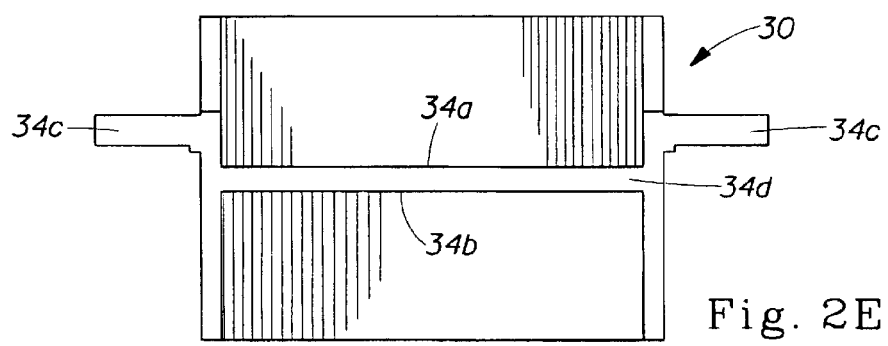
FIG. 2E is a rear view of the carriage main body.
Figure 2F:
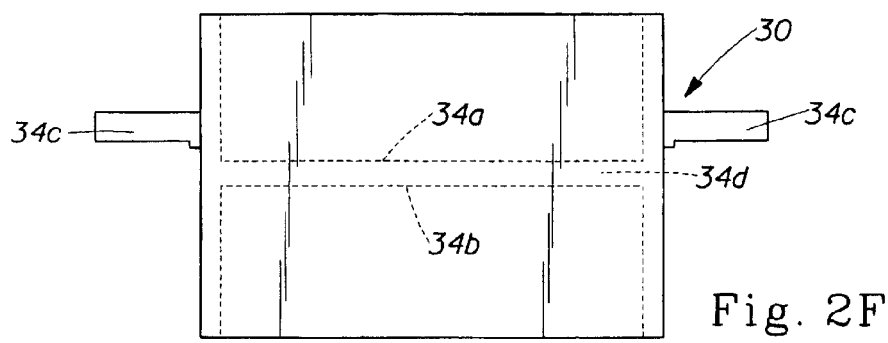
FIG. 2F is a front view of the carriage main body.
Figure 2G:
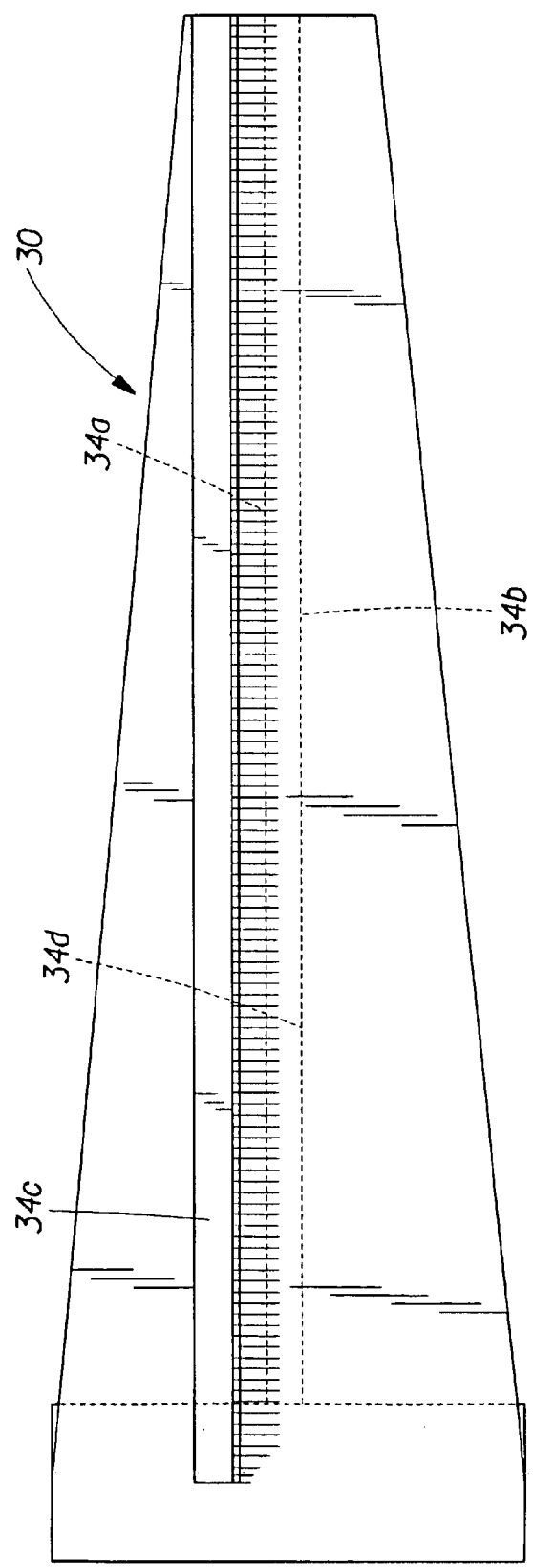
FIG. 2G is a side view of the carriage main body.

The apparatus 10 comprises a fixed main body 20 comprising a lower portion 22 and an upper portion 24 fixedly coupled to the lower portion 22, see FIGS. 1, 2A and 2B. The apparatus 10 further comprises a linearly reciprocating carriage 30 including a main body portion 34 positioned within a cavity 26 defined by the lower and upper portions 22 and 24 of the main body 20, see FIG. 2A, FIG. 2C (in FIG. 2C, the upper portion 24 has been removed from the lower portion 22 to illustrate the carriage 30), and FIGS. 2D–2G (in FIGS. 2D–2G, only the main body portion 34 is illustrated).

Figure 2H:
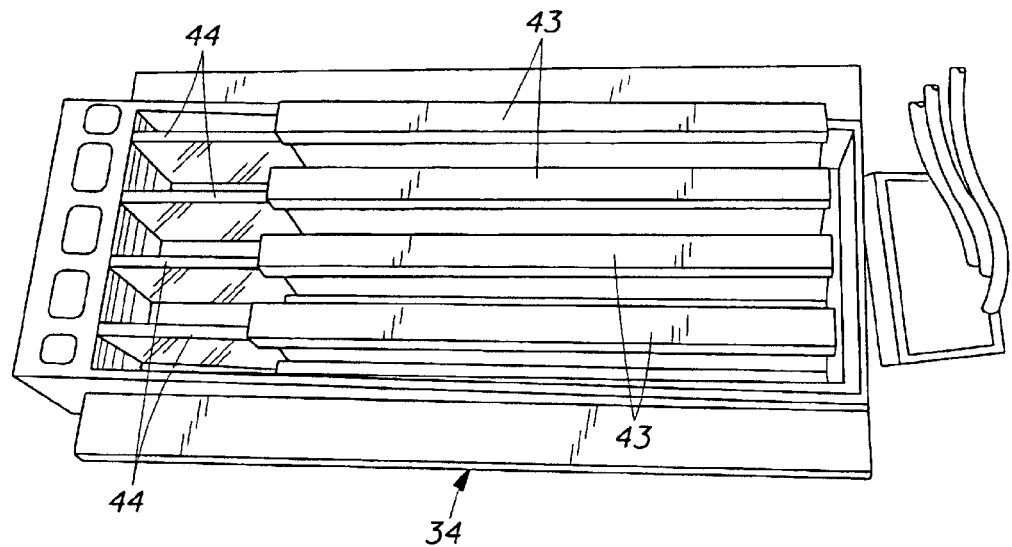
FIG. 2H is a perspective view of the carriage and motor second members.
Figure 2I:
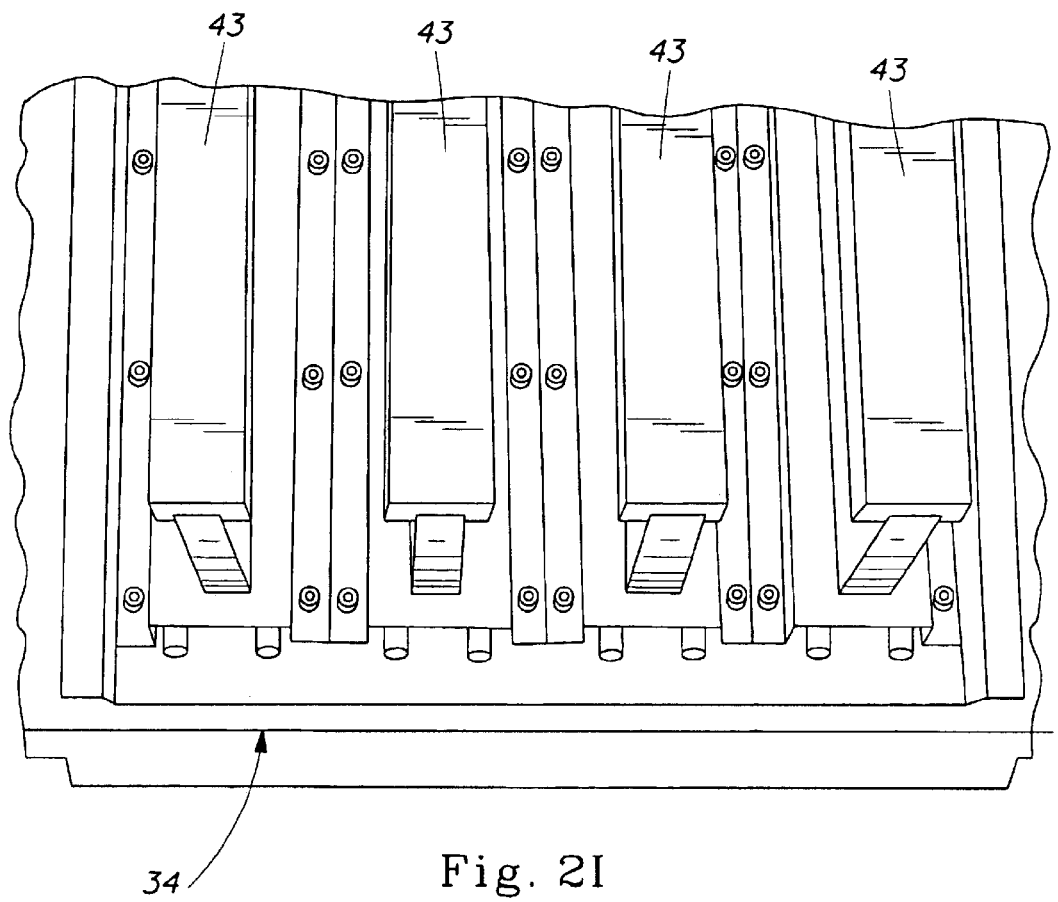
FIG. 2I is a perspective view of a portion of the carriage and motor second members.

The carriage 30 moves along first and second rails 28a and 28b via conventional linear bearings 32 mounted to a pair of wings 34c forming part of the carriage main body portion 34, see FIGS. 2A, 2C, 2D and 3A and 3B. Reciprocating movement of the carriage 30 is effected via eight separate servo linear motors 40 all working in conjunction, which motors 40 are commercially available from Rockwell International Corporation under the product designation "LEC-S-4P." Each servo motor 40 comprises a generally U-shaped first member 42 comprising a metal U-shaped element 42a having a plurality of magnets 42b mounted within and extending substantially the entire length of its U-shaped cavity, see FIGS. 2A and 4, and a movable second member 43 comprising a metal support plate having a plurality of coils wrapped about and extending along the length of the support plate, see FIGS. 2H and 2I. Four of the first members 42 are fixedly coupled to an inner surface 24a of the upper portion 24 of the main body 20, see FIG. 2A, while the remaining four first members (not shown) are fixedly coupled to an upper surface (not shown) of the lower portion 22 of the main body 20 just below the carriage 30. Four of the second members 43 are fixedly coupled to an upper portion 34a of a main plate 34d of the carriage main body portion 34, while the remaining four second members (not shown) are fixedly coupled to a lower portion 34b of the main plate 34d of the carriage main body portion 34. Four polymeric supporting plates 44 are mounted to the upper portion 34a of the main plate 34d, see FIG. 2A, and four polymeric supporting plates (not shown) are mounted to the lower portion 34b of the main plate 34d. The motor second members 43, fixedly coupled to the upper and lower portions 34a and 34b of the main plate 34d of the carriage main body portion 34, are mounted inline with the polymeric plates 44.

Upon actuation of the motors 40, each second member 43 moves relative to its corresponding first member 42 such that the carriage 30 linearly moves relative to the fixed main body 20. In the illustrated embodiment, the motors 40 are capable of moving the carriage 30 at a speed up to +/−3 meters/second, and at an acceleration rate up to +/−196 m/s$^2$; and cause the carriage 30 to generate a loading force, i.e., the force applied by the second plate 200 against web material sample and the first plate 100, of up to about +/−20,000 Newtons.

Figure 11:
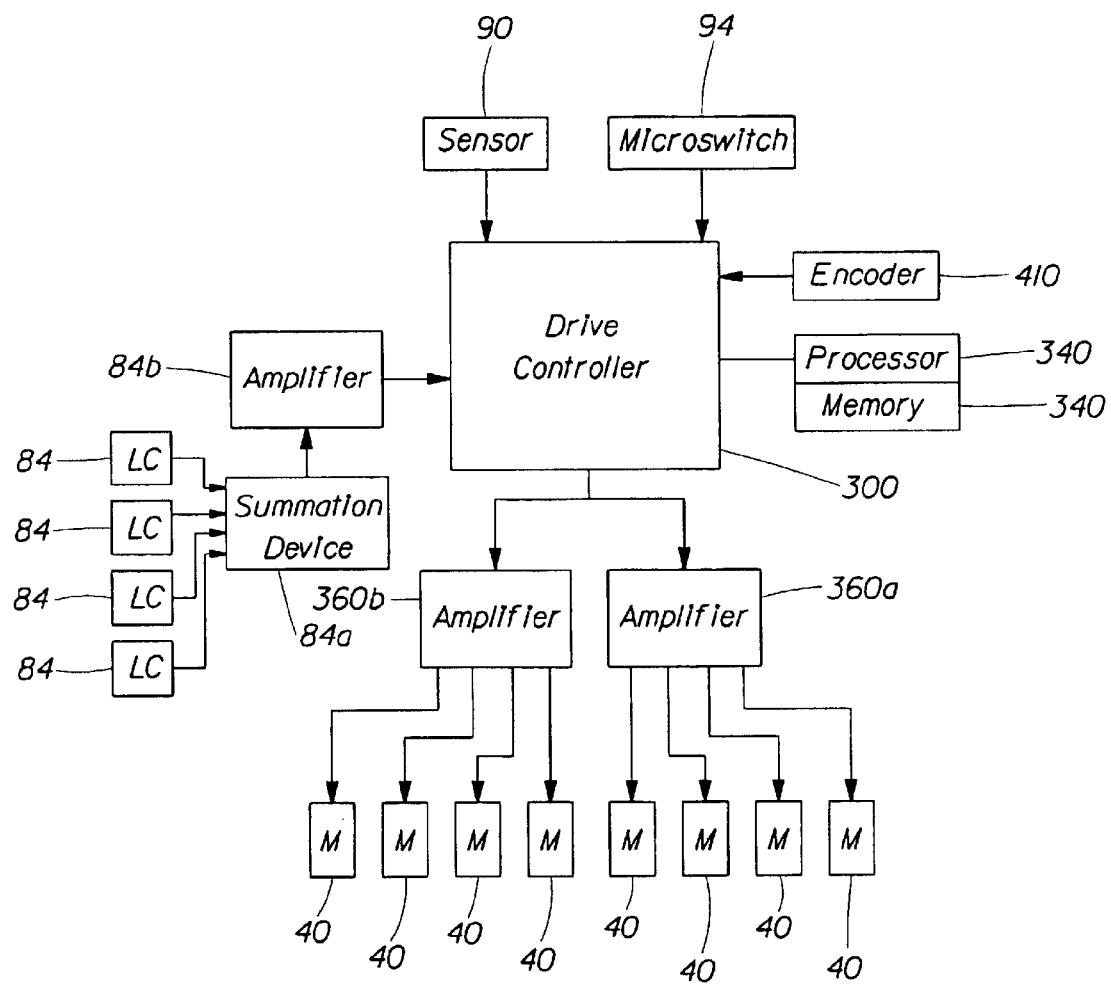
FIG. 11 is a block diagram illustrating a driver controller and amplifiers for driving the motors of the apparatus of FIG. 1.

A drive controller 300, one of which is commercially available from Delta Tau Corporation under the product designation "Turbo PMAC 2-PC," is provided for controlling the operation of the motors 40, see FIG. 11. The drive controller 300 generates a drive signal, which is received by first and second amplifiers 360a and 360b. The amplifiers 360a and 360b are commercially available from Delta Tau Corporation under the product designation "Quad Amp." Each amplifier 360a, 360b is connected to four servo motors 40. In response to receiving the drive signal from the controller 300, each amplifier 360a, 360b generates substantially the same drive control signal to its corresponding four motors 40.

The position of the carriage 30 relative to the fixed main body 20 is sensed via a linear encoder read head 410 coupled to the upper portion 24 of the fixed main body 20, see FIGS. 2A, which reads a position value from a corresponding sensor strip 412 mounted to the carriage 30 for movement with the carriage 30.

Figure 3A:
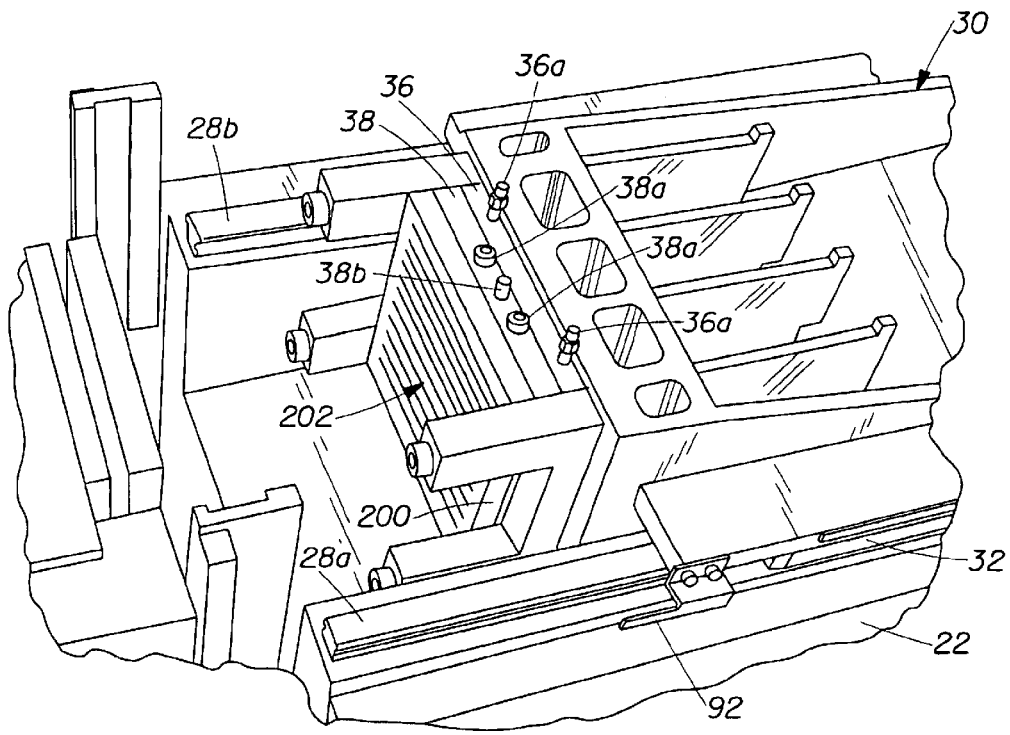
FIG. 3A is a perspective view of a portion of the carriage and the second plate mounted to the carriage.
Figure 3B:
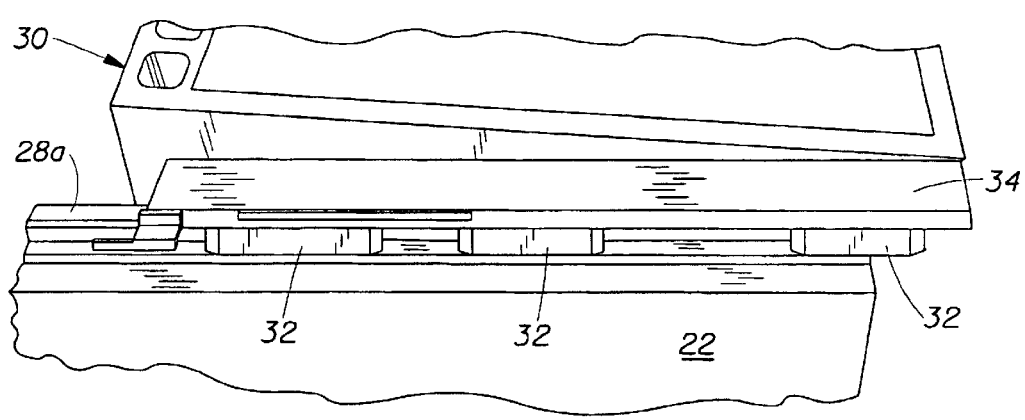
FIG. 3B is a side, perspective view of a portion of the carriage and a portion of the main body lower portion.
Figure 4:
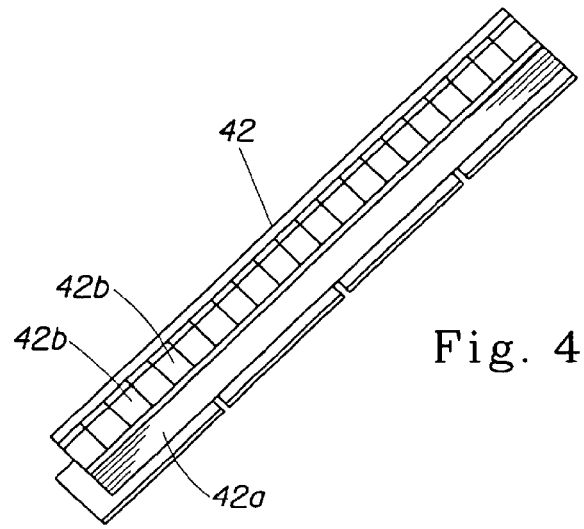
FIG. 4 is a perspective view of a U-shaped first member of one of the servo linear motors in the apparatus of FIG. 1.
Figure 11A:
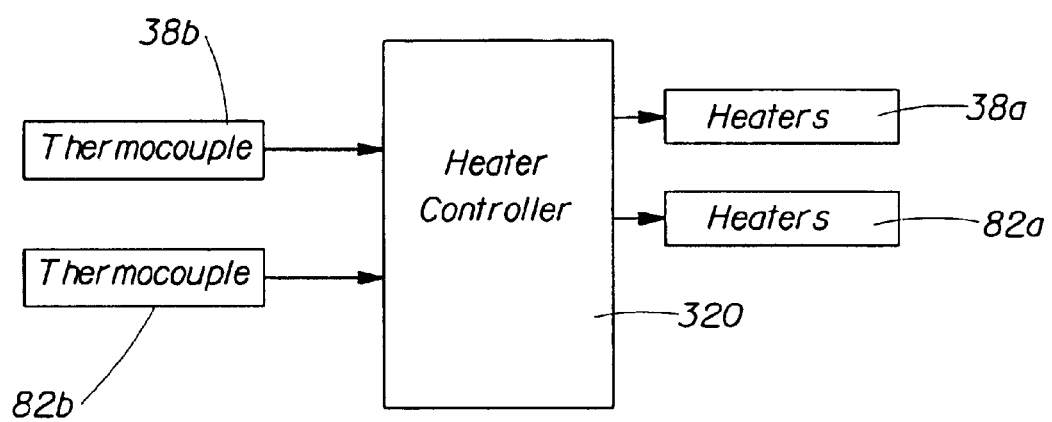
FIG. 11A is a block diagram illustrating a heater controller of the present invention.

The carriage 30 further comprises a cooled plate 36 and a heated plate 38, see FIGS. 2A and 3A. The second plate 200 is mounted, such as bolts (not shown), directly to the heated plate 38. The plate 38 is heated via a pair of resistive heaters 38a, see FIGS. 2A and 3A. The temperature of the plate 38 is detected via a thermocouple 38b, which generates temperature signals to a heater controller 320, see FIGS. 2A and 11A. The heater controller 320 controls activation of the resistive heaters 38a so as to maintain the plate 38 at a desired temperature. The cooled plate 36 is cooled via air circulating through the plate 36. The air is provided to the plate 36 via a pair of air lines coupled to the plate 36 via fittings 36a, see FIG. 3A. The cooled plate 36 prevents energy in the form of heat from being transferred from the heated plate 38 to the carriage main body portion 34.

A pair of spring-biased rear bumpers 50 are provided to limit the travel of the carriage 30 in a direction away from the first plate 100, see FIG. 1.

Referring again to FIG. 1, the lower portion 22 of the main body 20 comprises an outer support member 22a. Extending through the support member 22a are, in the illustrated embodiment, four threaded bores (not shown), each provided with a corresponding threaded rod 60, see FIGS. 6 and 7. Fixedly coupled to the outer support member 22a are a pair of L-shaped position limiting members 22b and 22c. A spring-loading plate 70 is received between the members 22b and 22c and abuts against the threaded rods 60. A spring-loaded base plate 72 is also received between the members 22b and 22c and is biased against arm portions 22d of the limiting members 22b and 22c via a plurality of compression springs 74, see FIGS. 5–7 and 6A. A pair of alignment rods 72a extend from the plate 72 and pass through linear bearings 70a provided in the spring-loading plate 70 as well as linear bearings (not shown) provided in the support member 22a, see FIG. 7. The springs 74 are mounted on corresponding rods extending from the spring-loaded plate 72. Bores are provided in the spring-loading plate 70 for receiving the rods about which the springs 74 are mounted. The position of the spring-loading plate 70 can be varied via adjustment of the positions of the threaded rods 60 so as to adjust the biasing force applied by the springs 74 against the plate 72. In the illustrated embodiment, approximately twelve (12) springs 74 are provided for applying approximately 7000 pounds (31,000 N) of force against the spring-loaded plate 72.

A cooled plate 80 is fixedly coupled to the spring-loaded plate 72 via bolts (not shown), see FIGS. 5–7 and 6A. A heated plate 82 is fixedly mounted to the cooled plate 80 via preload screws. Positioned between the cooled plate 80 and the heated plate 82 are a plurality of piezoelectric load cells 84, four in the illustrated embodiment, see FIGS. 6A and 7, which are commercially available along with the preload screws for joining the heated plate 82 to the cooled plate 80 from Kistler Instrument Corporation under the product designation "Load Washer and Preload Screw, Model No. 9031." Signals generated by the load cells 84 are provided to a summation device 84a, see FIG. 11, which is commercially available from Kistler Corporation under the product designation "4-Gang Connector, Model No. 107B." The summation device 84a functions to combine the signals generated by the four load cells 84 and generate a single force signal to an amplifier 84b. The amplifier 84b is commercially available from Kistler Corporation under the product designation "Dual Charge Amplifier, Model No. 5010B." An amplified force signal is generated by the amplifier 84b to the controller 300 and is representative of the combined force directly applied to the load cells 84 by the cooled plate 80 as a result of the first and second plates 100 and 200 engaging a web material sample S. The preload screws coupling the heated plate 82 to the plate 80 extend through center bores in the load cells 84.

Figure 5:
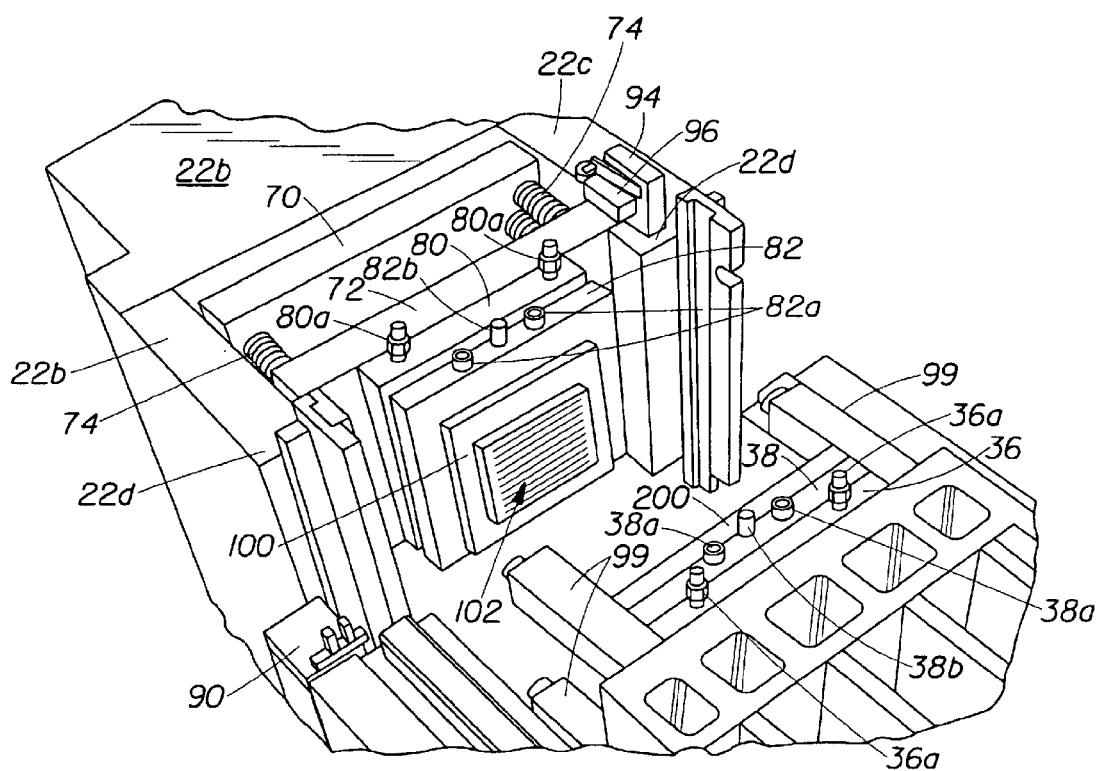
FIG. 5 is a perspective view of an outer support member of the apparatus main body, L-shaped position limiting members; a spring-loading plate, a spring-loaded plate, a heated plate, a cooled plate and a stationary first plate of the apparatus illustrated in FIG. 1.
Figure 6:
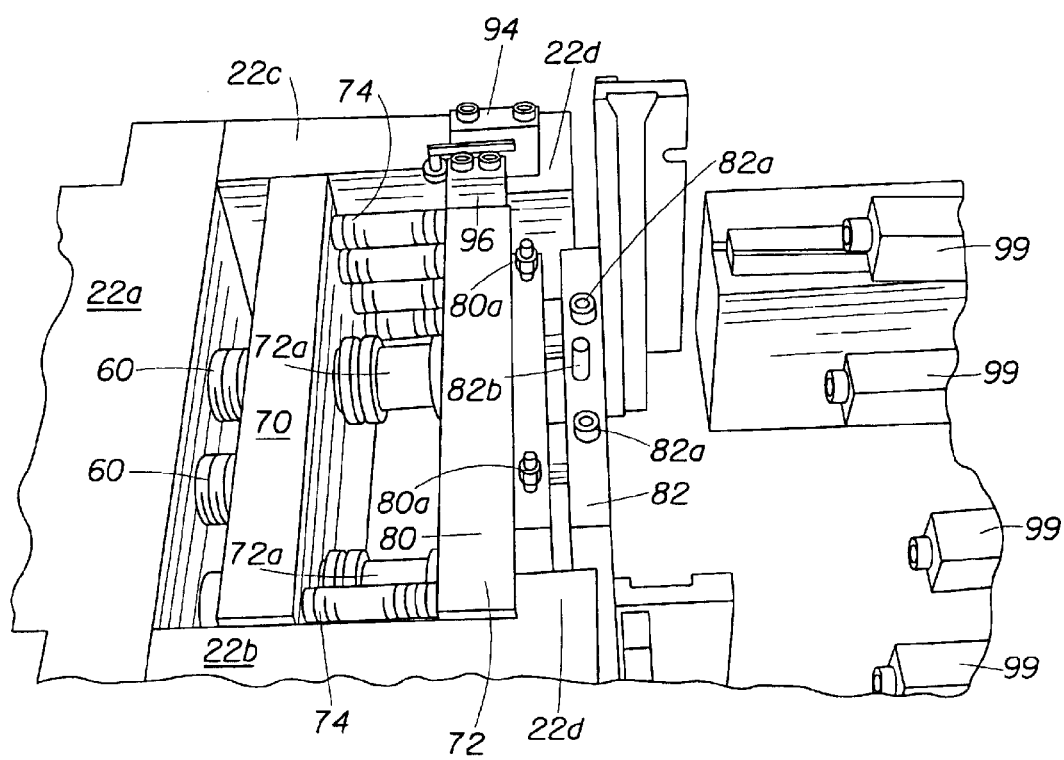
FIGS. 6 and 7 are perspective views of the outer support member of the apparatus main body, the L-shaped position limiting members, the spring-loading plate, the spring-loaded plate, the heated plate, and the cooled plate and, wherein the stationary first plate is not illustrated.
Figure 6A:
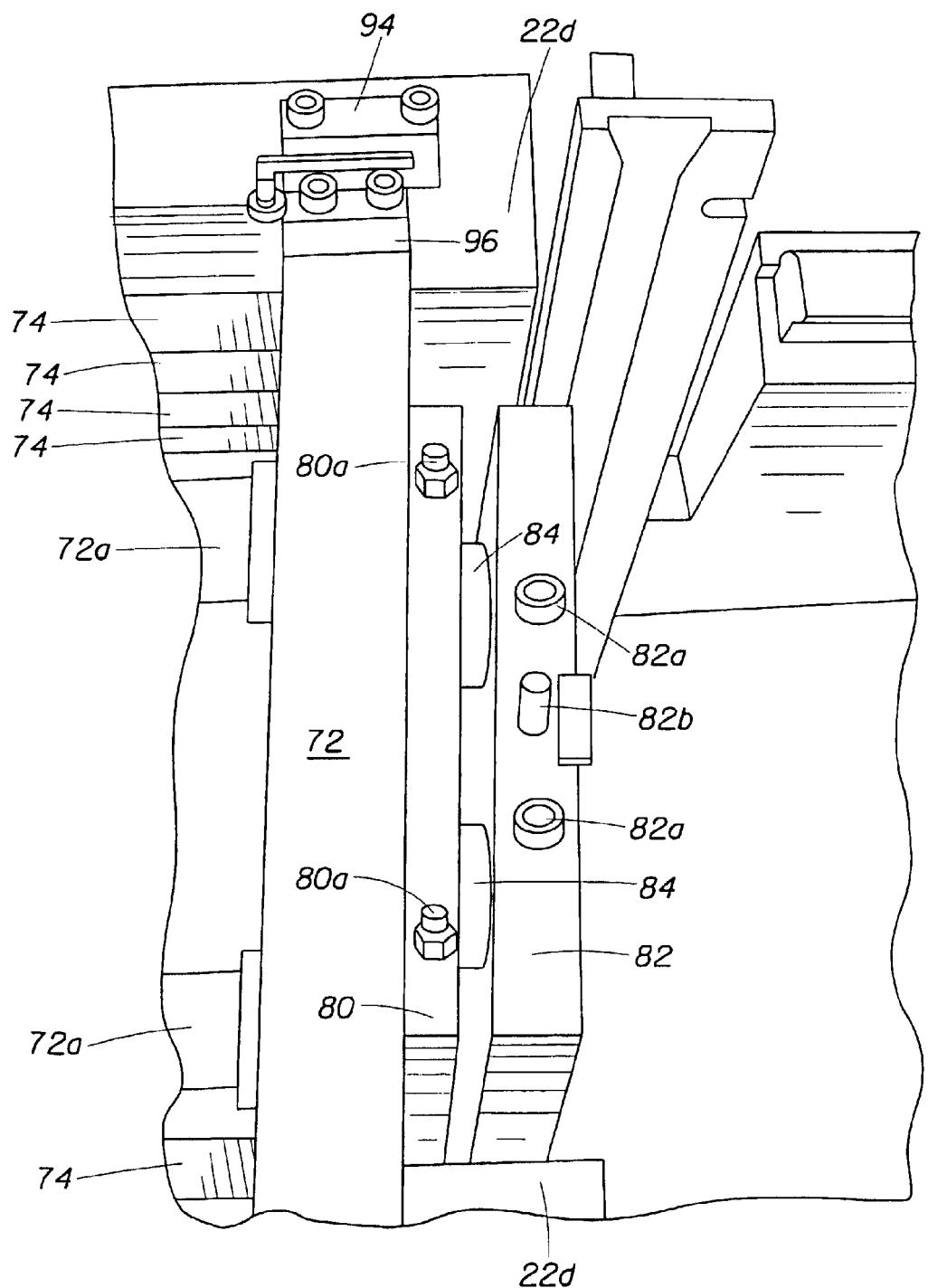
FIG. 6A is a perspective view of portions of the L-shaped position limiting members; the spring-loaded plate, the heated plate, and the cooled plate and, wherein the stationary first plate is not illustrated.
Figure 7:
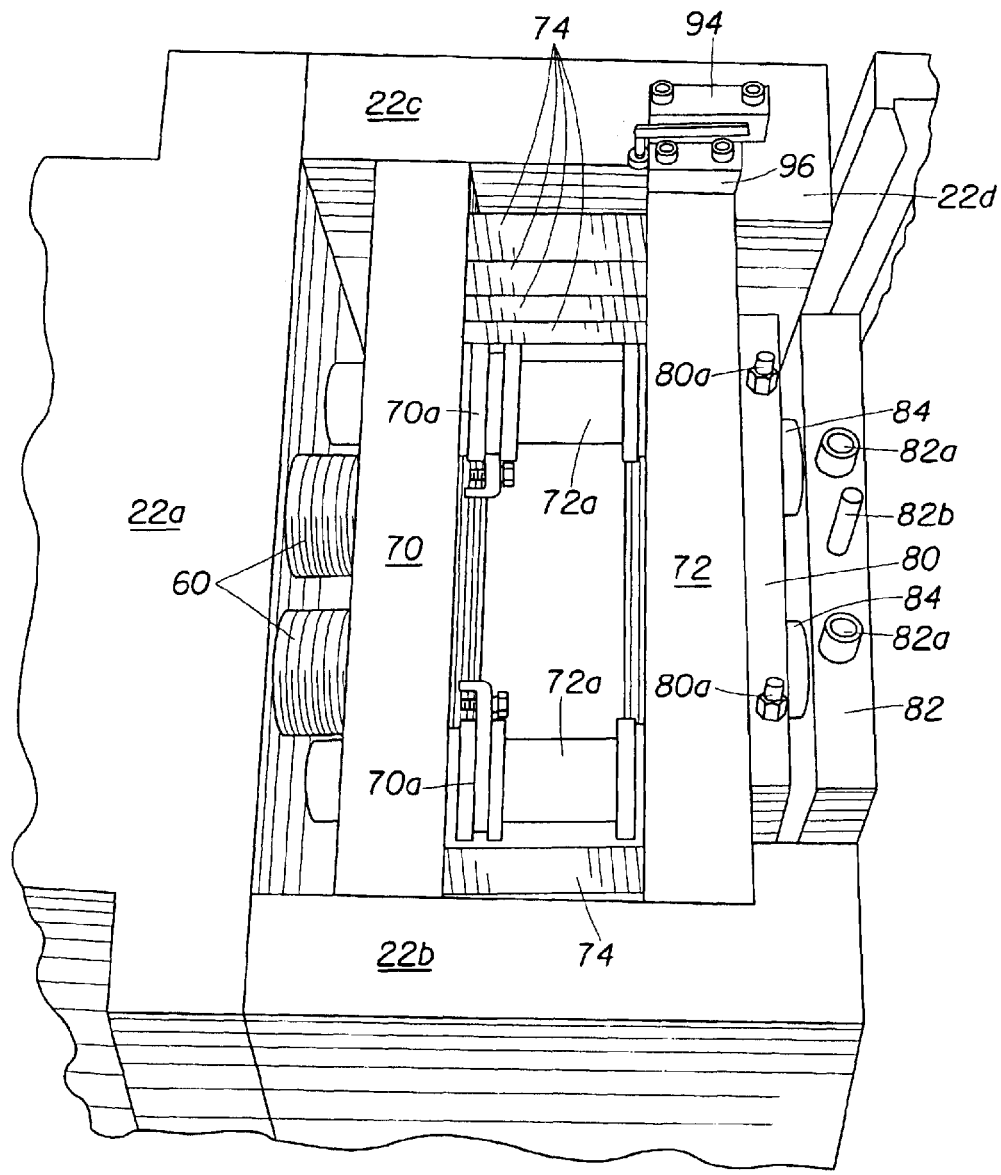

The first plate 100, illustrated in FIG. 5 but not shown in FIGS. 6, 7 and 6A, is mounted, such as by bolts (not shown), directly to the heated plate 82. The plate 82 is heated via a pair of resistive heaters 82a, see FIGS. 5, 6 and 6A. The temperature of the plate 82 is detected via a thermocouple 82b, which generates temperature signals to the controller 320, see FIGS. 6, 6A and 11A. The heater controller 320 controls activation of the resistive heaters 82a so as to maintain the plate 80 at a desired temperature. The cooled plate 80 is cooled via air circulating through the plate 80. The air is provided to the plate 80 via a pair of air lines coupled to the plate 80 via fittings 80a. The cooled plate 80 prevents energy in the form of heat from being transferred from the heated plate 82 to the spring-loaded plate 72.

To prevent damage to the first and second plates 100 and 200 due to over travel of the carriage 30 towards the first plate 100, a sensor 90 is mounted to the lower portion 22 of the main body 20 and a flag 92 is mounted to the main body portion 34 of the carriage 30, see FIGS. 2A, 3A and 5. The sensor 90 is coupled to the controller 300, see FIG. 11. If the carriage 30 moves too far in a direction towards the first plate 100, the flag 92 on the carriage 30 will actuate the sensor 90, which generates a corresponding signal to the controller 300. In response, the controller 300 terminates power to the motors 40 driving the carriage 30. A second sensor arrangement for preventing damage to the first and second plates 100 and 200 is also provided. It comprises a microswitch 94 mounted to the limiting member 22c and an actuator 96 fixedly mounted to the spring-loaded plate 72, see FIGS. 6 and 7. The microswitch 94 is coupled to the controller 300, see FIG. 11. Engagement arms 99 (not shown in FIGS. 2A and 2D–2G) are mounted to the main body portion 34 of the carriage 30, see FIGS. 5 and 6, and are adapted to engage the spring-loaded plate 72 prior to the first and second teeth 102 and 202 on the first and second plates 100 and 200 being fully engaged, i.e., prior to the second teeth 202 engaging bottom portions on the first plate 100 between the first teeth 102. When the force applied by the engagement arms 99 against the spring-loaded plate 72 exceeds the biasing force applied by the compression springs 74 against the plate 72, the plate 72 will move in a direction toward the spring-loading plate 70 causing the actuator 96 to actuate the switch 94, which, in turn, generates a corresponding signal to the controller 300. In response, the controller 300 disconnects power to the motors 40 driving the carriage 30.

During a ring rolling operation, first teeth $T_A$ on a first roll $R_1$ engage with second teeth $T_B$ on a second roll $R_2$, see FIG. 8. A given point on a web material WM moving at a web velocity Vw is engaged by the first and second teeth $T_A$ and $T_B$ for a time period 2T as it moves through the nip N defined by the first and second rolls $R_1$ and $R_2$. One-half of the total engagement time that the given point on the web material is engaged by the first and second teeth $T_A$ and $T_B$ can be determined via the following equation:

$$T = a\cos\left[1 - \frac{E_M}{Di}\right] \cdot \left[\frac{Di}{2 \times Vw}\right]$$

where:

$E_M$ is equal to the maximum depth of engagement of the first and second teeth $T_A$ and $T_B$;

Di is equal to the diameter of the first and second rolls $R_1$ and $R_2$ (it is presumed that the rolls $R_1$ and $R_2$ have the same diameter); and and Vw is equal to the web velocity.

The depth of engagement of first and second teeth $T_A$ and $T_B$ engaging the given point on the web material WM as a function of time is defined by the following equation:

$$E(t) = E_M - Di \cdot \left[1 - \cos\left[a\cos\left(1 - \frac{E_M}{Di}\right) \cdot \left(\frac{t}{T} - 1\right)\right]\right]$$

$E_M$ is equal to the maximum depth of engagement of the first and second teeth $T_A$ and $T_B$;

Di is equal to the diameter of the first and second rolls $R_1$ and $R_2$ (it is presumed that the rolls $R_1$ and $R_2$ have the same diameter);

t is equal to the process time and has a value from 0 to 2T; and

T is equal to one-half of the total time the given point on the web material WM is engaged by teeth $T_A$ and $T_B$ on the first and second rolls $R_1$ and $R_2$, see the equation above.

Figure 10:
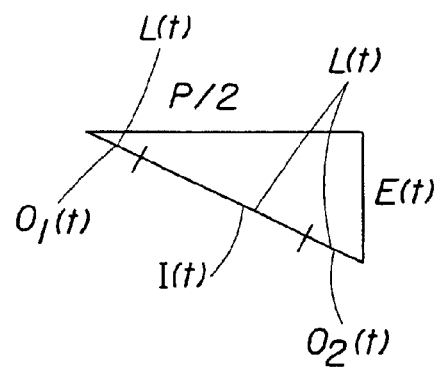
FIG. 10 is a schematic illustration of various dimensions illustrated in FIG. 9.

The engagement rate change or tooth tip velocity Ve is determined by the following equation:

$$Ve = \frac{d}{dt}E(t) = -Di \cdot \sin\left[a\cos\left(1 - \frac{E_M}{Di}\right) \cdot \left(\frac{t}{T} - 1\right)\right] \cdot \left[\frac{a\cos\left(1 - \frac{E_M}{Di}\right)}{T}\right]$$

where:

$E_M$ is equal to the maximum depth of engagement of the first and second teeth $T_A$ and $T_B$, see FIG. 10;

t is equal to the process time and has a value from 0 to 2T;

T is equal to one-half of the total time the given point on the web material WM is engaged by teeth $T_A$ and $T_B$ on the first and second rolls $R_1$ and $R_2$, see the equation above; and Di is equal to the diameter of the first and second rolls $R_1$ and $R_2$ (it is presumed that the rolls $R_1$ and $R_2$ have the same diameter.

The tooth tip acceleration Ae is determined by the following equation:

$$Ae = \frac{d^2}{dt^2}E(t) = -Di \cdot \cos\left[a\cos\left(1 - \frac{E_M}{Di}\right) \cdot \left(\frac{t}{T} - 1\right)\right] \cdot \left[\frac{a\cos\left(1 - \frac{E_M}{Di}\right)}{T}\right]^2$$

where:

$E_M$ is equal to the maximum depth of engagement of the first and second teeth $T_A$ and $T_B$;

t is equal to the process time and has a value from 0 to 2T;

T is equal to one-half of the total time the given point on the web material WM is engaged by teeth $T_A$ and $T_B$ on the first and second rolls $R_1$ and $R_2$, see the equation above; and Di is equal to the diameter of the first and second rolls $R_1$ and $R_2$ (it is presumed that the rolls $R_1$ and $R_2$ have the same diameter.

A ring rolling process is simulated by the apparatus 10 of the present invention in the following manner.

Prior to running the simulation, an engineer/technician defines the following parameters concerning the ring rolling operation to be simulated: a desired web velocity Vw, i.e., the velocity at which the web material WM would run if passed between a pair of ring rolling rolls $R_1$ and $R_2$; a maximum depth of engagement $E_M$ of the first and second teeth $T_A$ and $T_B$ on the ring rolling rolls $R_1$ and $R_2$; the pitch p of the first and second teeth $T_A$ and $T_B$ on the first and second rolls $R_1$ and $R_2$; and the diameter Di of the first and second rolls $R_1$ and $R_2$.

Figure 12A:
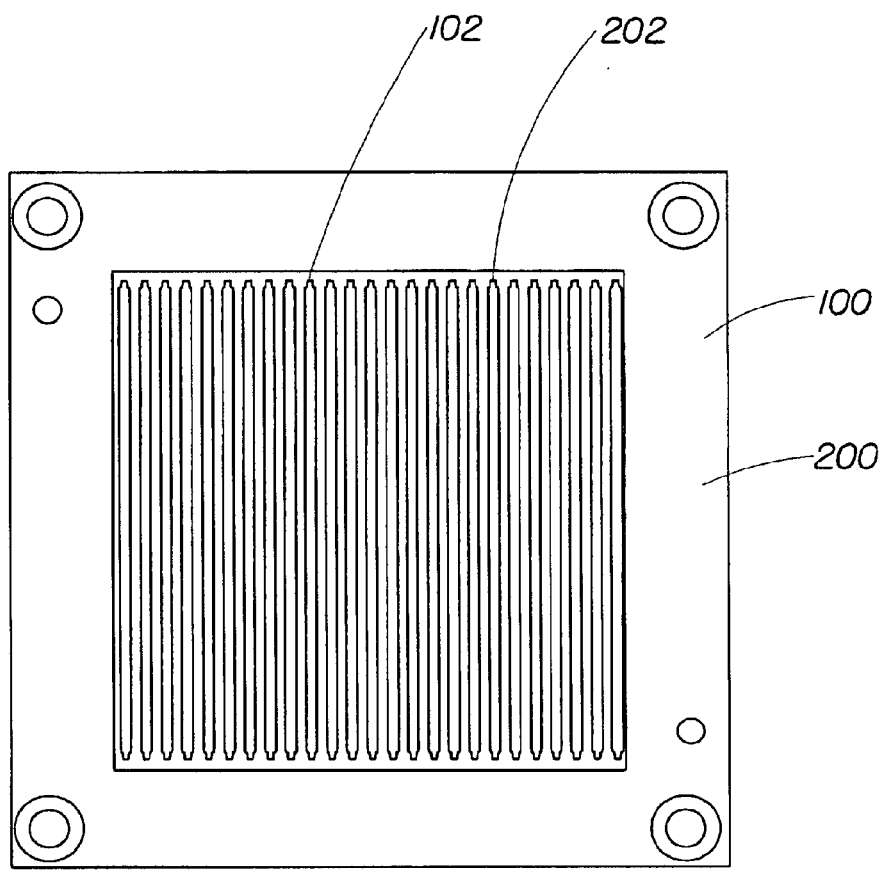
FIG. 12A is a top view of the first, second plate of the apparatus of FIG. 1.
Figure 12B:
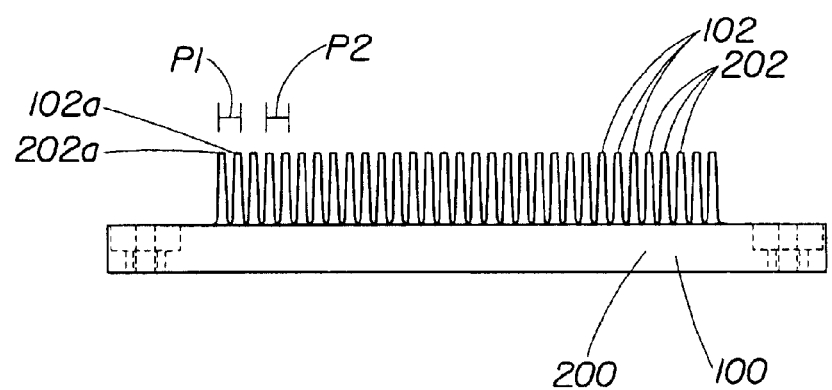
FIG. 12B is a side view of the first, second plate of the apparatus of FIG. 1.

The first plate 100 is provided with first teeth 102 spaced apart at a first pitch $p_1$ and the second plate 200 is provided with second teeth 202 spaced apart at a second pitch $p_2$, see FIGS. 12A and 12B. In the illustrated embodiment, the first and second pitches $p_1$ and $p_2$ are equal to one another. The first and second pitches $p_1$ and $p_2$ are also equal to the pitches of the first and second teeth $T_A$ and $T_B$ on the ring rolling rolls $R_1$ and $R_2$, the operation of which is to be simulated. Each first tooth 102 has an outer tip portion 102a having a first radius RT1 corresponding to the radius of the first teeth $T_A$ on the first ring rolling roll $R_1$ and each outer second tip portion 202a has a second radius RT2 corresponding to the radius of the second teeth $T_B$ on the second ring rolling roll $R_2$, see FIG. 9. The first and second radii RT1 and RT2 are presumed to equal one another.

Figure 13A:
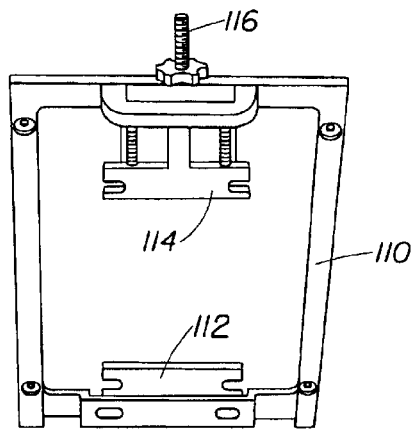
FIG. 13A is a perspective view of a web material sample holder.
Figure 13B:
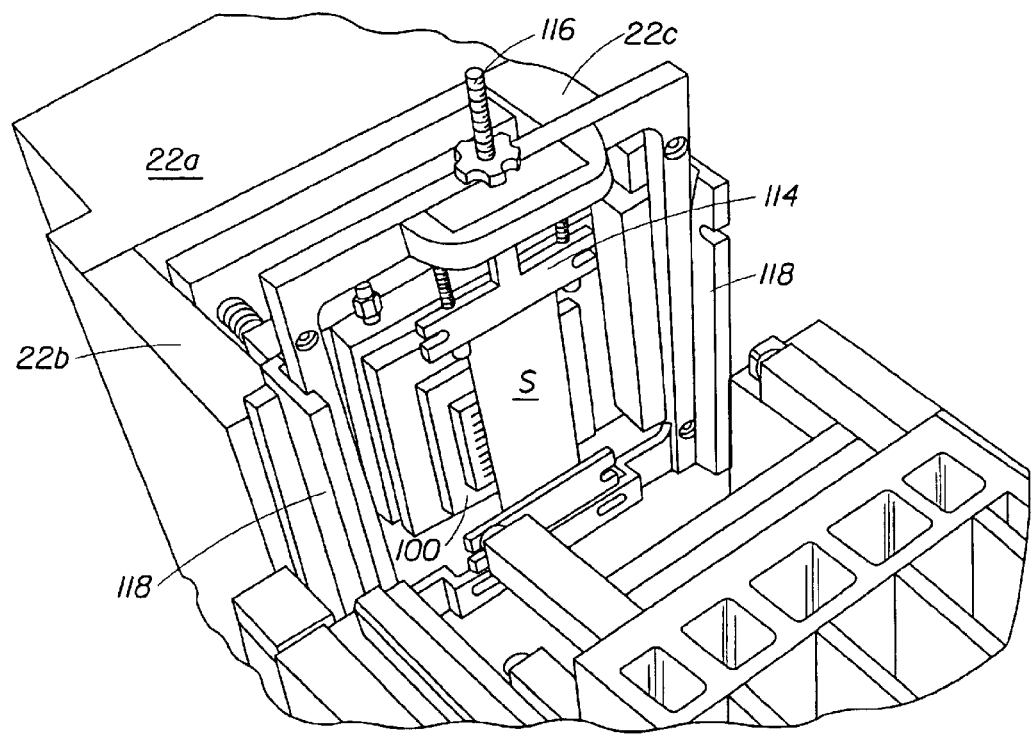
FIG. 13B is a perspective view of the sample holder illustrated in FIG. 13A mounted in first and second receiving members which, in turn, are fixedly mounted to the lower main body portion.

A substantially rectangular sample S of a web material WM to be tested is mounted in a holder 110, preferably at a predefined tension, see FIGS. 13A–13B. The holder 110 comprises a stationary mounting member 112 and a movable mounting member 114. Once the sample S is mounted to or gripped by the mounting members 112 and 114, the movable member 114 may be moved via a screw 116 or other mechanism so as to apply a desired tension to the sample S. The holder 110 is mounted in first and second receiving members 118, which, in turn, are fixedly mounted to the lower portion 22 of the fixed main body 20.

Prior to engaging the web material sample S with the plates 100 and 200, the sample S may be heated to a predefined temperature by moving the carriage 30 to a position such that the second teeth 202 on the second plate 200 are positioned just adjacent to the web material sample S. As noted above, the heater controller 320 maintains the heated plates 38 and 82 at a predefined temperature. The sample S can be heated to a desired temperature by maintaining the sample S between the first and second plates 100 and 200 for a predefined period of time with the heated plates 38 and 82 controlled to a predetermined temperature.

The drive controller 300 controls the operation of the servo linear motors 40 in accordance with feedback generated by the load cells 84 and the linear encoder read head 410, see FIG. 11. The controller 300 causes the motors 40 to drive the carriage 30 from a home position toward the first plate 100 such that the first and second plates 100 and 200 engage the sample S and, further, such that the second teeth 202 on the second plate 200 move to a desired engagement depth relative to the first teeth 102 on the first plate 100. When the second teeth 202 have been moved to the desired engagement depth relative to the first teeth 102, the first and second teeth 102 and 202 are substantially parallel to one another and interdigitated. The controller 300 then causes the motors 40 to drive the carriage 30 in a direction away from the first plate 100 such that the teeth 202 of the second plate 200 disengage from the web material sample S and, further, such that the carriage 30 returns to its home position. In the illustrated embodiment, movement of the carriage 30 from its home position to a position where the teeth 202 on the second plate 200 are positioned to a desired depth relative to the teeth 102 on the first plate 100 is separated into four discrete segments: a forward acceleration segment; a forward linear segment; a forward transition segment; and an engagement segment. Further, movement of the carriage 30 from the position where the teeth 202 on the second plate 200 are positioned to a desired depth relative to the teeth 102 on the first plate 100 back to its home position is separated into four discrete segments: a disengagement segment; a reverse transition segment; a reverse linear segment; and a reverse acceleration segment.

Each of the eight segments comprises a plurality of equal discrete time intervals, e.g., 300 microseconds. For example, the total time period required for execution of the eight segments is determined and this total time period is then divided by a predefined number of control points the drive controller 300 is capable of processing during a ring rolling simulation operation, e.g., 7990, so as to determine the period for the discrete time intervals. If the calculated period for the discrete time intervals is less than a predefined value, e.g., 300 micro-seconds, the predefined value is used.

Using equations corresponding to the eight segments, to be discussed below, a processor/memory unit 340 determines, for each discrete time interval within each segment, a corresponding position for the carriage 30. The time intervals and corresponding carriage positions are provided to the drive controller 300. During the forward acceleration segment, the forward linear segment, the forward transition segment, the reverse transition segment, the reverse linear segment and the reverse acceleration segment, the drive controller 300 generates appropriate drive signals to the amplifiers 360a, 360b to control the movement of the carriage 30 based on the corresponding, predefined carriage positions, and in response to carriage position signals from the linear encoder read head 410. During the engagement and disengagement segments, the drive controller 300 generates appropriate drive signals to the amplifiers 360a, 360b to control the movement of the carriage 30 based on the corresponding, predefined carriage positions, and in response to carriage position signals from the linear encoder read head 410 and force signals from the amplifier 84b.

The engagement segment is defined as occurring just after the carriage 30 has reached its "0 position," i.e., the position of the carriage 30 just as the second teeth 202 cross a plane separating the first and second teeth 102 and 202, until the teeth 202 on the second plate 200 are positioned at a desired depth $E_M$ relative to the first teeth 102 on the first plate 100. The disengagement segment is defined as occurring when the carriage 30 reverses its direction so as to move the second plate 200 away from the first plate 100 until the carriage reaches its "0 position." The processor/memory unit 340 calculates a carriage position, a tooth tip velocity Ve and a tooth tip acceleration Ae for each of a plurality of equal discrete time intervals occurring during the engagement and disengagement segments as follows.

Using the equation for one-half of the total engagement time T, set out above, and the predefined values for the ring rolling process to be simulated, the processor/memory unit 340 determines the engagement time T, which is equal to the time period for the engagement segment as well as the time period for the disengagement segment. The time T for each of the engagement and disengagement segments is then divided into a plurality of equal discrete time intervals, each of which has a period calculated as discussed above. For each time interval, an engagement depth E is calculated by the processor/memory unit 340 using the equation set out above for E(t). From each calculated engagement depth E, the processor/memory unit 340 determines a corresponding carriage position. The processor/memory unit 340 also determines for the engagement segment an initial tooth tip velocity and an initial tooth tip acceleration, using the equations set out above for Ve and Ae. It further determines for the disengagement segment a final tooth tip velocity and a final tooth tip acceleration, using the equations set out above for Ve and Ae. It then provides the discrete time intervals and corresponding carriage positions to the motor controller 300, which stores the information in memory.

Once the carriage 30 reaches its "0 position," the controller 300 causes the servo linear motors 40 to continue to drive the carriage 30 toward the first plate 100 such that the first and second plates 100 and 200 engage the sample S and, further, such that the second teeth 202 on the second plate 200 move to a desired engagement depth $E_M$ relative to the first teeth 102 on the first plate 100. In generating appropriate drive signals to the amplifiers 360a, 360b, the controller 300 takes into consideration position feedback information from the linear encoder read head 410 such that it compares the actual position of the carriage 30 determined from the position information provided by the read head 410 to the predefined, desired positions. The controller 300 also takes into consideration force information generated by the load cells 84 in generating appropriate drive signals to the amplifiers 360a, 360b.

It was found that when a web sample S was not provided between the plates 100 and 200, and the second plate 200 was moved such that its teeth 202 were positioned to a desired depth relative to the first teeth 102, carriage position could be accurately controlled to a tolerance of about +/−10 microns without requiring force feedback information from the load cells 84. This is because no force is applied by the second plate 200 to the first plate 100 during the engagement and disengagement segments since the second teeth 202 never contact the first teeth 102 even though the second teeth 202 move to the desired engagement depth $E_M$ relative to the first teeth 102. When a web material sample S is provided, a load is generated during engagement of the web material sample S by the first and second teeth 102 and 202. This load should be offset by the motors 40 so as to achieve accurate carriage position control to a small tolerance such as from about +/−10 microns to about +/−35 microns. Hence, the controller 300 increases the drive signal provided to the amplifiers 360a, 360b so that the force generated by the motors 40 to the carriage 30 is increased by an amount substantially equal to the magnitude of the force sensed by the load cells 84.

Linear movement of the second plate 200 relative to the first plate 100 in accordance with the discrete time intervals and corresponding engagement depths E results in work being done to the sample S simulating work which would have been done to the sample S had the sample S passed through a pair of ring rolling rolls $R_1$ and $R_2$. Controlled movement of the carriage 30 by the controller 300 typically results in the outer tip portions 202a of the second teeth 202 following a position vs. time curve such as the one illustrated in FIG. 14A. The zero position 0 is just as the second teeth 202 on the second plate 200 pass through a plane defined between the first and second teeth 102, 202.

Equations used by the processor/memory unit 340 to determined a carriage position (also referred to herein as "tooth tip position") for each discrete time interval, which intervals have the same period as the time intervals corresponding to the engagement and disengagement segments, and other parameters, will be provided for the remaining segments, namely, the forward acceleration segment; the forward linear segment; the forward transition segment; the reverse transition segment; the reverse linear segment; and the reverse acceleration segment. The unit 340 provides the time intervals and corresponding carriage positions to the drive controller 300 for these segments.

For the Engagement Segment, the processor/memory unit 340 initially determines, via the equation set out above for T, the time T required for the carriage 30 to move from its "0 position" to a position where the second teeth 202 on the second plate 200 are at a desired maximum engagement depth $E_M$ relative to the first teeth 102 on the first plate 100. Thereafter, the unit 340 divides the time T by the predefined time interval period, which period is determined as set out above, to determine a plurality of discrete time intervals for the Engagement Segment. The unit 340 then determines, for each discrete time interval, an engagement position or tooth tip position E (equal to a carriage position relative to the carriage "0 position"), a tooth tip velocity Ve (which is equal to the carriage velocity) and a tooth tip acceleration Ae (which is equal to the carriage acceleration), see the Example set out below where the total engagement time T is equal to 9.19 milliseconds.

The total time period for the forward transition segment is set to a predefined value, e.g., 3.1 milliseconds and, typically, the same time period is used for this segment during all ring rolling process simulations. The final tooth tip position (corresponds to a final carriage position relative to the carriage "0 position"), final tooth tip velocity, and final tooth tip acceleration for this segment are all equal to the initial tooth tip position, initial tooth tip velocity and initial tooth tip acceleration for the engagement segment, see the Example set out below. Further, the initial tooth tip acceleration for this segment must be 0. From these given values, the unit 340 determines initial and intermediate tooth tip positions, initial and intermediate tooth tip velocity values, and initial and intermediate tooth tip acceleration values for this segment.

During the Forward Linear Segment, the tooth tip acceleration (corresponds to the carriage acceleration) decreases to zero such that the tooth tip velocity is maintained at a constant value. This segment is used to buffer any jerking motion of the carriage 30 as it changes from a positive acceleration to a negative acceleration. The time period for this segment is set to a predefined value, e.g., 2.0 milliseconds, and typically the same time period is used for this segment during all ring rolling process simulations. The final tooth tip acceleration must be equal to zero and the final tooth tip velocity must equal the initial tooth tip velocity for the Forward Transition Segment, see the Example set out below.

During the Forward Acceleration Segment, the carriage 300 accelerates at a constant rate from a 0 velocity starting at a home position to a final velocity, which is equal to the initial velocity of the Forward Linear Segment. The carriage home position is defined by an engineer/technician and is relative to the carriage "0 position." Typically, it is equal to or nearly equal to the maximum distance the carriage 30 may be positioned away from its "0 position." In the Example set out below, it is set at 70 mm. The distance for this segment is equal to the distance the home position is spaced from the carriage "0 position" minus the distances the carriage 30 moves during the Forward Linear and Forward Transition Segments (8.485 mm in the Example). The time for this segment is not predefined. The unit 340 determines a positive constant acceleration (i.e., a tooth tip acceleration) required for the carriage 30 to be accelerated from a 0 velocity to a velocity equal to the initial tooth tip velocity for the Forward Linear Segment within the predefined distance for this segment.

For the Disengagement Segment, the processor/memory unit 340 initially determines, via the equation set out above for T, the time T required for the carriage 30 to move from its position where the second teeth 202 on the second plate 200 are at their maximum engagement depth $E_M$ relative to the first teeth 102 on the first plate 100 to its "0 position." Thereafter, the unit 340 divides the time T by the predefined time interval period, which period is determined as set out above, to determine a plurality of discrete time intervals for the Disengagement Segment. The unit 340 then determines, for each discrete time interval, an engagement position or tooth tip position E (equal to the carriage position from the "0 position"), a tooth tip velocity (which is equal to the carriage velocity) and tooth tip acceleration (which is equal to the carriage acceleration), see the Example set out below where the total time T for this segment is equal to 9.19 milliseconds.

The total time period for the Reverse Transition Segment is set to a predefined value, e.g., 3.1 milliseconds and, typically, the same time period is used for this segment during all ring rolling process simulations. The initial tooth tip position, initial tooth tip velocity, and initial tooth tip acceleration (In the Example and for the Reverse Transition, Linear and Acceleration Segments and the Disengagement Segment, a positive acceleration has a negative value and a negative acceleration has a positive value) for this segment are all equal to the final tooth tip position, final tooth tip velocity and final tooth tip acceleration for the Disengagement Segment, see the Example set out below. Further, the final tooth tip acceleration must be 0 at the end of the Reverse Transition Segment. From these given values, the unit 340 determines initial and intermediate tooth tip positions, initial and intermediate tooth tip velocity values and initial and intermediate tooth tip acceleration values for this segment.

During the Reverse Linear Segment, the tooth tip acceleration begins at zero and changes to a constant tooth tip deceleration value, which value is the constant tooth tip deceleration value for the Reverse Acceleration Segment to be discussed below. This segment is used to buffer any jerking motion of the carriage 30 as it changes from a positive acceleration to a negative acceleration. The time period for this segment is set to a predefined value, e.g., 2.0 milliseconds, and typically, is the same time period used for this segment during all ring rolling process simulations. The initial tooth tip velocity for this segment must equal the final tooth tip velocity for the Reverse Transition Segment, see the Example set out below.

During the Reverse Acceleration Segment, the carriage 300 decelerates at a constant rate from an initial velocity equal to the final velocity of the Reverse Linear Segment down to a 0 velocity, at which point the carriage is at its home position. The distance for this segment is equal to the distance the home position is spaced from the carriage "0 position" minus the distances the carriage 30 moves during the Reverse Linear and Reverse Transition Segments (8.485 mm in the Example). The time period for this segment is not predefined. The unit 340 determines a constant rate of deceleration (i.e., a tooth tip deceleration) required for the carriage 30 to be decelerated from a velocity equal to the final tooth tip velocity for the Reverse Linear Segment to a 0 velocity within the predefined distance for this segment.

The processor/memory unit 340 determines tooth tip positions, i.e. carriage positions, for each of the equal discrete time intervals as well as other parameters for the forward acceleration segment; the forward linear segment; the forward transition segment; the reverse transition segment; the reverse linear segment; and the reverse acceleration segment using the following equations:

Tfl=Time in the Forward Linear Segment; Predefined value, e.g., 0.0020 second;

Tft=Time in the Forward Transition Segment; Predefined value, e.g., 0.0031 second;

Pi1=Starting time for the engagement segment; Predefined value, e.g., 0.00;

Tbl=Time in the Reverse (Backward) Linear Segment; Predefined value, e.g., 0.0020 second;

Tbt=Time in the Reverse (Backward) Transition Segment; Predefined value, e.g., 0.0031 second;

$E_M$ is equal to the maximum depth of engagement of the first and second teeth 102 and 202;

Di is equal to the diameter of the first and second rolls $R_1$ and $R_2$ (it is presumed that the rolls $R_1$ and $R_2$ have the same diameter);

and Vw is equal to the web velocity;

Plim=Is equal to the distance between the carriage "0 position" and the carriage home position;

T=Ti=To; and

Npts=Total number of control points, all of the same period, during all segments, e.g., 7990.

Time to complete engagement segment (sec)

$$Ti = a\cos\left(1 - \frac{E_M}{Di}\right) \cdot \left[\frac{Di}{2 \cdot Vw}\right]$$

Time to complete disengagement segment (sec)

$$To = a\cos\left(1 - \frac{E_M}{Di}\right) \cdot \left[\frac{Di}{2 \cdot Vw}\right]$$

Initial engagement velocity (m/sec)

$$Vi1 = -Di \cdot \sin\left[a\cos\left(1 - \frac{E_M}{Di}\right) \cdot (-1)\right] \cdot \left[\frac{a\cos\left(1 - \frac{E_M}{Di}\right)}{Ti}\right]$$

Initial engagement acceleration (m)

$$Ai1 = -Di \cdot \cos\left[a\cos\left(1 - \frac{E_M}{Di}\right) \cdot (-1)\right] \cdot \left[\frac{a\cos\left(1 - \frac{E_M}{Di}\right)}{Ti}\right]^2$$

Initial velocity in the forward transition segment (m/sec)

$$Vft1 = Vi1 - \frac{Ai1 \cdot Tft}{2}$$

Jerk in the forward transition segment (m/sec³)

$$Kf = \frac{(Ai1 - 0)}{Tft}$$

Initial position in the forward transition segment (m)

$$Pft1 = Pi1 - Vft1 \cdot Tft - \frac{Kf \cdot Tft^2}{6}$$

Initial position in the forward linear segment (m)

$$Pfl1 = Pft1 - Vft1 \cdot Tfl$$

Time in the Forward Acceleration Segment (sec)

$$Tfa = \frac{(Pfl1 - P\lim)}{\frac{Vft1}{2}}$$

Acceleration in forward acceleration segment (m/sec²)

$$Afa = \frac{(Vft1 - 0)}{Tfa}$$

Total time in Forward Acceleration, Linear, Transition Segments and Engagement Segment (sec)

$$Tf = Ti + Tft + Tfl + Tfa$$

Total time in forward acceleration and forward linear segments $$Tfal = Tfa + Tfl$$

Total time in the forward acceleration, forward linear and forward transition segments (sec)

$$Tfalt = Tfa + Tfl + Tft$$

Final disengagement position (m)

$$Po2 = E_M - Di \cdot \left[1 - \cos\left[a\cos\left(1 - \frac{E_M}{Di}\right) \cdot (1)\right]\right]$$

Final disengagement velocity (m/sec)

$$Vo2 = -Di \cdot \sin\left[a\cos\left(1 - \frac{E_M}{Di}\right) \cdot (1)\right] \cdot \left[\frac{a\cos\left(1 - \frac{E_M}{Di}\right)}{T}\right]$$

Final disengagement acceleration (m/sec²)

$$Ao2 = -Di \cdot \cos\left[a\cos\left(1 - \frac{E_M}{Di}\right) \cdot (1)\right] \cdot \left[\frac{a\cos\left(1 - \frac{E_M}{Di}\right)}{T}\right]^2$$

Jerk in the backward transition segment (m/sec³)

$$Kb = -\frac{(0 - Ao2)}{Tbt}$$

Final position in the backward transition segment (m)

$$Pbt2 = Po2 + Vo \cdot Tbt + \frac{(Ao2 \cdot Tbt^2)}{2} + \frac{(Kb \cdot Tbt^3)}{6}$$

Final velocity in the backward transition segment (m)

$$Vbt2 = Vo2 + \frac{Ao2}{2} \cdot Tbt$$

Final position in the backward linear position (m)

$$Pbl2 = Pbt2 + Vb2 \cdot Tbl$$

Time in the backward acceleration segment (sec)

$$Tba = \frac{(P\lim - Pbl2)}{\left(\frac{Vbt2}{2}\right)}$$

Acceleration in the backward acceleration segment (m/sec²)

$$Aba = \frac{Vbt2}{Tba}$$

Total time in the forward segments, engagement segment and disengagement segment (sec)

$$Tbo = Tf + To$$

Total time in the forward segments, engagement segment plus the disengagement and backward transition segments (sec)

$$Tbot = Tf + To + Tbt$$

Total time in the forward segments, engagement segment plus the disengagement, backward transition and backward linear segments (sec)

$$Tbotl = Tf + To + Tbt + Tbl$$

Total time in the forward and backward segments, and engagement and disengagement segments (sec)

$$Tfb = Tf + To + Tbt + Tbl + Tba$$

The period for the discrete time intervals (sec)

$$Tspl = \left(\frac{Tfb}{Npts}\right)$$

Position in forward acceleration segment (m); where t=0 to Tfa (sec)

$$Pfa = Plim + \frac{Afa \cdot t^2}{2}$$

Position in forward linear segment (m); where t=0 to Tfl (sec)

$$Pfl = Pfl1 + Vfl1 \cdot t$$

Position in forward transition segment (m); where t=0 to Tft (sec)

$$Pft = Pft1 = Vft1 \cdot t + \frac{Kf \cdot t^3}{6}$$

Position in engagement segment (m); where t=0 to Ti (sec)

$$Pi = E_M - Di \cdot \left[1 - \cos\left[a\cos\left(1 - \frac{E_M}{Di}\right) \cdot \left(\frac{t}{T} - 1\right)\right]\right]$$

Position in disengagement segment (m); where t=To to 2·To (sec)

$$Po = E_M - Di \cdot \left[1 - \cos\left[a\cos\left(1 - \frac{E_M}{Di}\right) \cdot \left(\frac{t}{T} - 1\right)\right]\right]$$

Position in backward transition segment (m); where t=0 to Tbt (sec)

$$Pbt = Po2 + Vo \cdot t + \frac{Ao2 \cdot t^2}{2} + \frac{Kb \cdot t^3}{6}$$

Position in backward linear segment (m); where t=0 to Tbl (sec)

$$pbl = Pbl1 + Vbl \cdot t$$

Position in backward acceleration segment (m); where t=0 to Tba (sec)

$$Pba = Pbl2 + Vbt2 \cdot t + \frac{Aba \cdot t^2}{2}$$

Figure 15:
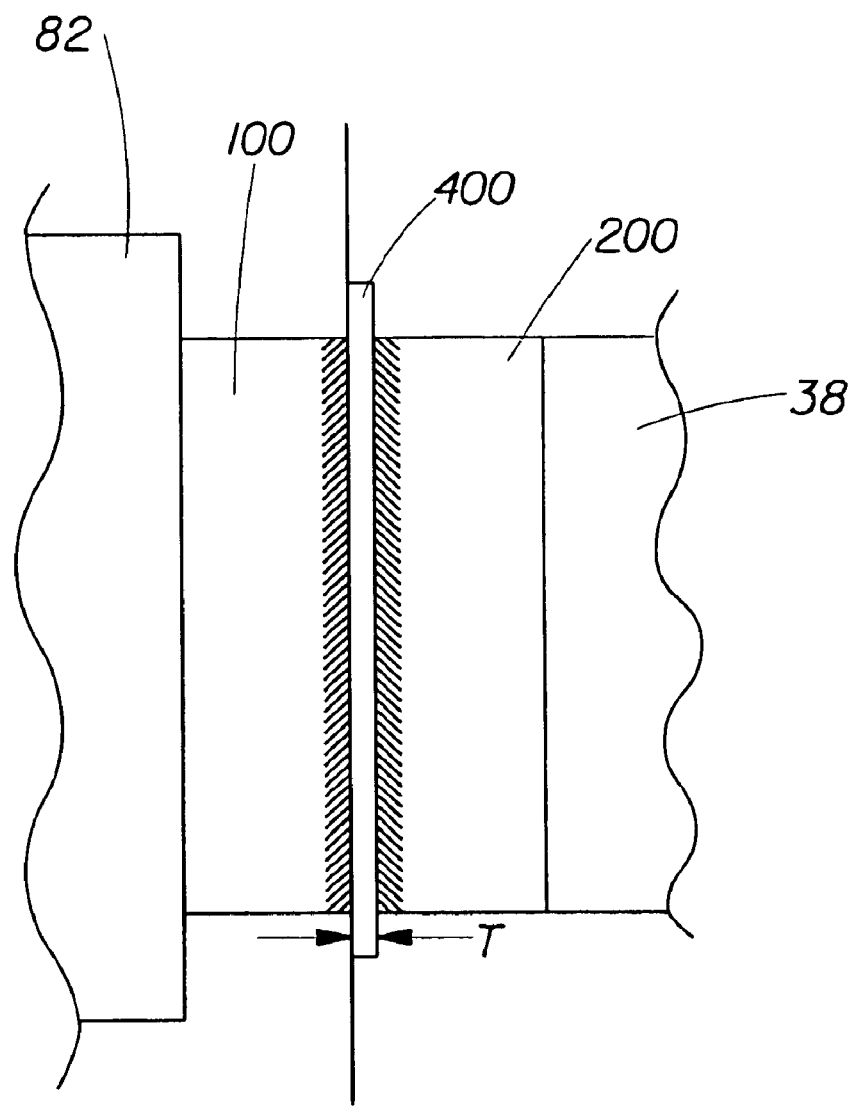
FIG. 15 is a side view of a calibration plate being engaged by the first and second plates of the apparatus of FIG. 1.

Prior to conducting a test operation, a calibration plate 400, having a known thickness T, is positioned adjacent to the first plate 20, see FIG. 15. The controller 300 controls the movement of the second plate 200 so that it slowly moves toward the first plate 100 until it engages the calibration plate 400. At the point of engagement, a position error of the servo linear motors 40 increases because movement of the carriage 30 is blocked by the calibration plate 400, which increase in position error is detected by the controller 300. That is, the controller 300 determines from position signals generated by the linear encoder read head 410 that the position of the carriage 30 is not changing even though the controller 300 is generating a drive signal to provide power to the motors 40. In response to sensing 0 movement of the carriage 30, the controller 300 knows that the carriage 30 is positioned a distance equal to the thickness of the calibration plate 400 away from a "0 position" for the carriage 30, i.e., the position of the carriage 30 just as the second teeth 202 on the second plate 200 cross a plane separating the teeth 102 and 202 on the first and second plates 100 and 200, respectively, see FIG. 15. The controller 300, based upon a position signal generated by the linear encoder read head 410 after reading the corresponding position value from the sensor strip 412, defines the current position of the carriage 30 as being a distance away from the "0 position" equal to the thickness of the calibration plate 400.

Strain (t) and strain rate experienced by the sample S during engagement by the first and second plates 100 and 200 can be determined using equations which will be developed with reference to FIGS. 9 and 10.

In FIG. 9, a first tooth 102 and a second tooth 202 on the first and second plates 100 and 200, respectively, (it is presumed that the pitch (p) of the first teeth 102 is the same as the pitch (p) of the second teeth 202) are shown engaged with a web material WM. A portion of the web material $WM_P$ extends between a center point $C_A$ on the first tooth 102 to a center point $C_B$ on the second tooth 202. The depth to which the teeth 102 and 202 are engaged is defined by E(t), see FIGS. 9 and 10, the equation for which is set out above. The initial length of the web portion $WM_P$, prior to being stretched by the teeth 102 and 202, is equal to one-half of the pitch p of the teeth 102 and 202, i.e., p/2. Processed or stretched length of the web material portion $WM_P$ as a function of time, i.e., L(t), see FIGS. 9 and 10, is determined using the following equation:

$$L(t) = O_1(t) + O_2(t) + I(t)$$

where $O_1(t)$ is equal to a section of the web material portion $WM_P$ engaged by the tooth 102 and extending from the tooth center point $C_A$ to a final tooth tangent point $C_{f1}$;

where $O_2(t)$ is equal to a section of the web material portion $WM_P$ engaged by the tooth 202 and extending from the tooth center point $C_B$ to a final tooth tangent point $C_{f2}$; and I(t) is equal to an intermediate section of the web portion $WM_P$ not engaged by either tooth 102, 202 and extending between the final tooth tangent points $C_{f1}$ and $C_{f2}$.

I(t) is defined by the following equation:

$$I(t) = \sqrt{(p/2)^2 + (E(t) - 2r)^2 - (2r)^2}$$

where:

p is equal to the pitch of the teeth 102 and 202;

r is equal to the radius RT1 of the outer tip portion 102a of the tooth 102 and is also equal to the radius RT2 of the outer tip portion 202a of the tooth 202, see FIG. 9, as radii RT1 and RT2 are presumed to be equal; and E(t) is equal to the depth to which the teeth 102 and 202 have engaged one another as a function of time, and is determined by the equation set out above.

$$O(t) = O_1(t) + O_2(t).$$

When E(t)−2r>0, O(t) is defined by the following equation:

$$O(t) = \left[\pi - a\cos\sqrt{\frac{(2r)^2}{(E(t) - 2r)^2 + (p/2)^2}} - \right.$$

-continued $$a\sin\sqrt{\frac{(p/2)^2}{(E(t)-2r)^2+(p/2)^2}}\Bigg]\cdot r$$

When $E(t)-2r<0$, $O(t)$ is defined by the following equation:

$$O(t)=\Bigg[-a\cos\sqrt{\frac{(2r)^2}{(E(t)-2r)^2+(p/2)^2}}+a\sin\sqrt{\frac{(p/2)^2}{(E(t)-2r)^2+(p/2)^2}}\Bigg]\cdot r$$

where:

p is equal to the pitch of the teeth 102 and 202;

r is equal to the radius RT1 of the outer tip portion 102a of the tooth 102 and is also equal to the radius RT2 of the outer tip portion 202a of the tooth 202, see FIG. 9, as radii RT1 and RT2 are presumed to be equal; and E(t) is equal to the depth to which the teeth 102 and 202 have engaged one another as a function of time, and is determined by the equation set out above.

When $E(t)-2r>0$, $S(t)$ is defined by the following equations:

$$\text{Strain}(t)=\left(\frac{2\cdot O(t)+I(t)}{p/2}-1\right)$$

$$\text{Strain}(t)=\left(\frac{\left(\pi-a\cos\sqrt{\frac{(2r)^2}{(E(t)-2r)^2+(p/2)^2}}-a\sin\sqrt{\frac{(p/2)^2}{(E(t)-2r)^2+(p/2)^2}}\right)\cdot}{p/2}\right)-1$$

When $E(t)-2r<0$, $S(t)$ is defined by the following equations:

$$\text{Strain}(t)=\left(\frac{2\cdot O(t)+I(t)}{p/2}-1\right)$$

$$\text{Strain}(t)=\left(\frac{\left(-a\cos\sqrt{\frac{(2r)^2}{(E(t)-2r)^2+(p/2)^2}}+a\sin\sqrt{\frac{(p/2)^2}{(E(t)-2r)^2+(p/2)^2}}\right)\cdot}{p/2}\right)-1$$

where:

p is equal to the pitch of the teeth 102 and 202;

r is equal to the radius RT1 of the outer tip portion 102a of the tooth 102 and is also equal to the radius RT2 of the outer tip portion 202a of the tooth 202, see FIG. 9, as radii RT1 and RT2 are presumed to be equal; and E(t) is equal to the depth to which the teeth 102 and 202 have engaged one another as a function of time, and is determined by the equation set out above.

The average strain rate (1/seconds) can be determined by taking the first derivative of Strain(t). The first derivative of Strain(t) can be derived using, for example, a commercially available math processing software package such as Mathcad.

Final strain ($S_f$) is defined by the following equation:

$$S_f=[(L_f-L_0)/L_0]$$

where $L_f$ is the final length, after processing, of a web material portion $WM_P$; and $L_0$ is the initial length, prior to processing, of that same web material portion $WM_P$.

$S_f$ is determined using the equation for Strain(t) with t=T.

It is believed that the first and second plates 100 and 200 of the apparatus 10 of the present invention can engage a web material sample S and stretch the sample S at a strain rate up to about 2000/seconds.

Tensile force applied to the web material sample S by the teeth 102 and 202 can be determined from the following equations:

For $(E(t)-2*r)>0$ $$F_{Mat}=\frac{F_{LC}}{\cos\left[a\sin\left[\frac{\left(\frac{p}{2}\right)^2}{\left(\frac{p}{2}\right)^2+(E(t)-2\cdot r)^2}\right]^{0.5}+a\cos\left[\frac{(2\cdot r)^2}{\left(\frac{p}{2}\right)^2+(E(t)-2\cdot r)^2}\right]^{0.5}-\frac{\pi}{2}\right]}$$

where $F_{LC}$ is equal to the combined force applied to the load cells 84;

p is equal to the pitch of the teeth 102 and 202;

r is equal to the radius RT1 of the outer tip portion 102a of the tooth 102 and is also equal to the radius RT2 of the outer tip portion 202a of the tooth 202, see FIG. 9, as radii RT1 and RT2 are presumed to be equal; and E(t) is equal to the depth of engagement of the first and second teeth 102 and 202 at a time t, where t has a value from 0 to 2T, see the equation above.

For $(E(t)-2*r)\leq 0$ $$F_{Mat}=\frac{F_{LC}}{\cos\left[\frac{\pi}{2}-a\sin\left[\frac{\left(\frac{p}{2}\right)^2}{\left(\frac{p}{2}\right)^2+(E(t)-2\cdot r)^2}\right]^{0.5}+a\cos\left[\frac{(2\cdot r)^2}{\left(\frac{p}{2}\right)^2+(E(t)-2\cdot r)^2}\right]^{0.5}\right]}$$

where:

$F_{LC}$ is equal to the combined force applied to the load cells 84;

p is equal to the pitch of the teeth 102 and 202;

r is equal to the radius RT1 of the outer tip portion 102a of the tooth 102 and is also equal to the radius RT2 of the outer tip portion 202a of the tooth 202, see FIG. 9, as radii RT1 and RT2 are presumed to be equal; and E(t) is equal to the depth of engagement of the first and second teeth 102 and 202 at a time t, where t has a value from 0 to 2T, see the equation above.

It is also contemplated that an engineer/technician can use the apparatus 10 of the present invention to simulate a desired strain and strain rate which a web material might experience during a ring rolling operation. The engineer/technician must define the following parameters: desired strain; desired strain rate; the pitch of the first and second teeth $T_A$ and $T_B$ on the first and second ring rolling rolls $R_1$ and $R_2$; the radius of the outer tip portions of the teeth $T_A$ and $T_B$; and the diameter Di of the first and second rolls $R_1$ and $R_2$. From the equations set out above for one-half of the total engagement time T; engagement as a function of time E(t); and strain S(t), further equations can then be developed to determine: web velocity Vw, i.e., the velocity at which the web material WM would run if passed between a pair of ring rolling rolls $R_1$ and $R_2$; maximum depth of engagement of the first and second teeth $T_A$ and $T_B$ on the ring rolling rolls $R_1$ and $R_2$; and one-half of the total engagement time T. Those values are then used to determine a plurality of positions for the carriage for discrete time periods using the equations set out above corresponding to the forward acceleration segment; the forward linear segment; the forward transition segment; the engagement segment; the disengagement segment; the reverse transition segment; the reverse linear segment; and the reverse acceleration segment so as to simulate a ring rolling operation where a web material is worked by engaging teeth at the desired strain rate.

The apparatus 10 of the present invention is also capable of varying the load applied by a first tool or workpiece mounted to the carriage 30 to a second tool or workpiece mounted to the spring-loaded plate 72 as a function of time. It is further contemplated that a workpiece may be mounted between the carriage 30 and the spring-loaded plate 72 and placed in tensile as a result of the carriage 30 being moved in a direction away from the spring-loaded plate 72. Control of the tensile force amount applied to the workpiece may be based on the position of the carriage 30 as a function of time or tensile loading of the workpiece as a function of time.

It is also contemplated that the spring constant for a spring or a workpiece including a portion defining a spring may be determined as follows. The spring (not shown) is mounted to the spring-loaded plate 72. Current to the motors 40 is varied as a function of time. For each predefined current amount, readings from the load cells 84 and a carriage position reading via the linear encoder read head 410 are taken. From the force readings generated by the load cells 84 and the displacement of the carriage 30 determined from the carriage position readings, which carriage displacement is equal to the displacement of the spring, the spring constant is determined.

Figure 14:
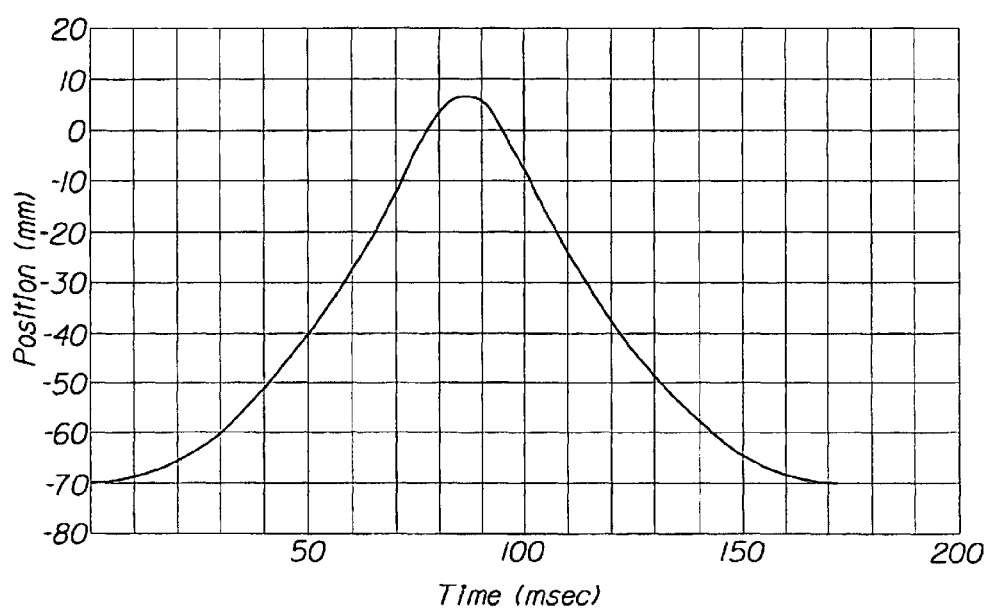
FIG. 14A is a plot of a position by time profile for the Example.
FIG. 14B is a plot of a velocity by time profile for the Example.
FIG. 14C is a plot of an acceleration by time profile for the Example.
Figure 14B:
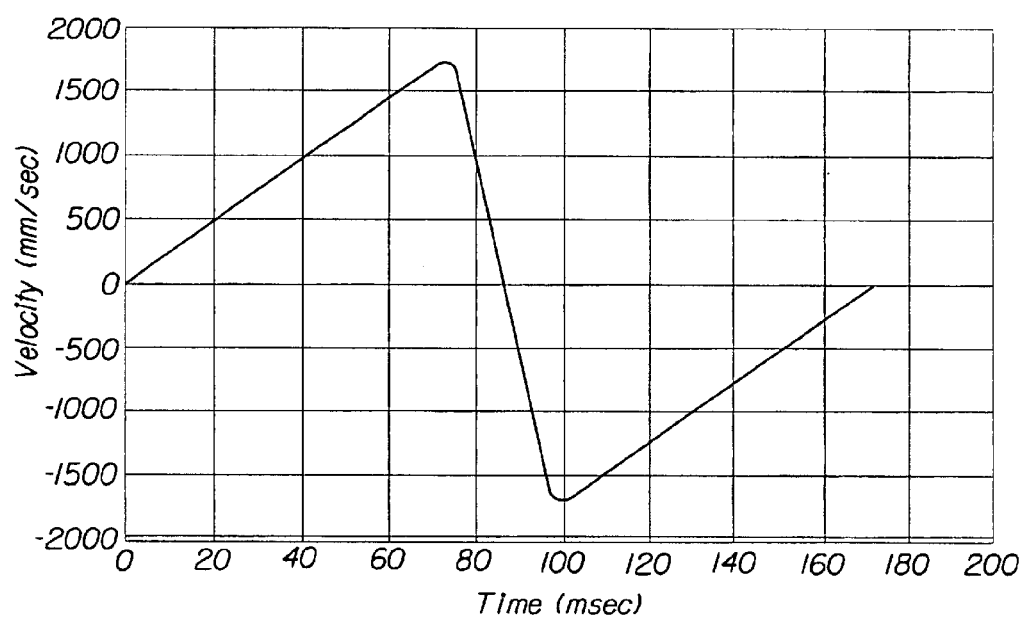
Figure 14C:
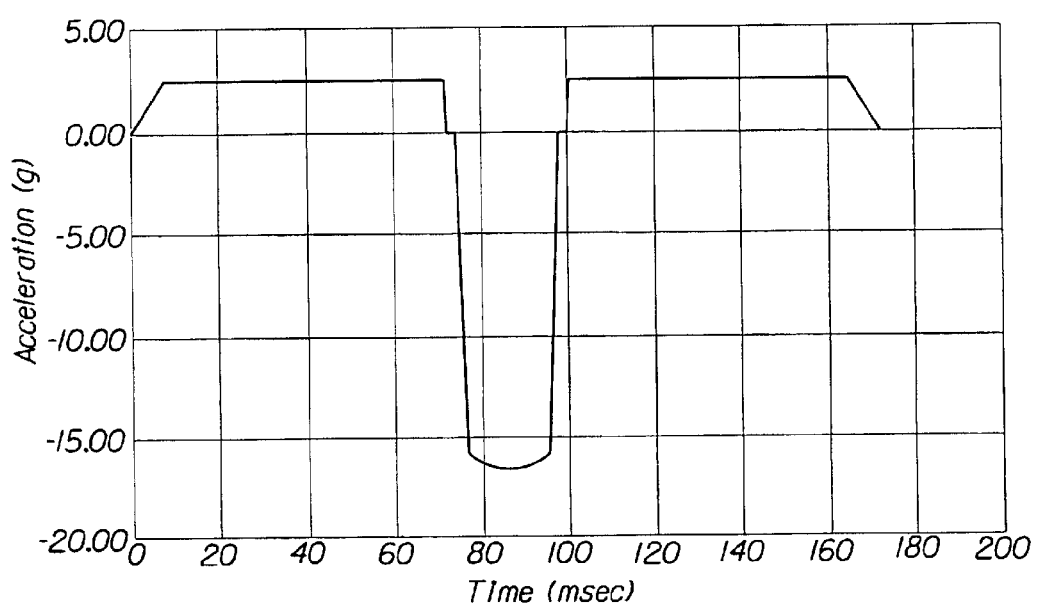

Data from an Example ring rolling simulation operation is set out below. A position by time profile for the Example is illustrated in FIG. 14A; a velocity by time profile for the Example is illustrated in FIG. 14B; and an acceleration by time profile for the Example is illustrated in FIG. 14C (1 g=9.8 m/s$^2$).

Data from Example

| High Speed Research Press Model for Rotary Nip Processes | | |
|---|---|---|
| Gravitational Acceleration, G (mm/sec2) | 9814.56 | Assumed distance for |
| Accel. + Linear + Transition Distance, Da (mm) | 70 | Acceleration Segment |
| Engagement Distance, De (mm) | 6.812 | 268.19 mils |
| Entering Roll Diameter, DrA (mm) | 152.40 | 6.0 inches |
| Exiting Roll Diameter, DrB (mm) | 152.40 | 6.0 inches |
| Web Speed, V (m/sec) | 2.4890 | 490 ft/min |

Note: numbers in the box above are process variables

| Calculation for Transition Segment | Forward | Reverse | |
|---|---|---|---|
| Initial acceleration in Trans. Segm. (mm/sec^2) | 0 | 0 | |
| Final acceleration in Trans. Segm. (mm/sec^2) | -155333.6 | -155333.6 | |
| Final speed in Transition Segment (mm/sec) | 1471.66 | 1471.66 | |
| Initial speed in Transition Segment (mm/sec) | 1712.42 | 1712.42 | |
| Acceleration Segment Distance (mm) | 61.52 | 61.52 | |
| Transition Segment Distance (mm) | 5.060 | 5.060 | |
| Time Spent in Linear Segment (msec) | 2.0 | 2.0 | Constant Values |
| Time spent in Transition Segment (msec) | 3.1 | 3.1 | |
| Linear Segment Distance (mm) | 56.46 | 56.46 | |
| Jerk in Transition Segment (mm/sec^3) | -50107615.6 | -50107615.6 | |

| Forward Acceleration Segment | | | | | |
|---|---|---|---|---|---|
| Acceleration Time (msec) | Acceleration Distance (mm) | Total Time (msec) | Position at Time (mm) | Tooth Tip Velocity (mm/sec) | Tooth Tip Acceleration (g's) |
| 0.00 | 0.00 | 0.00 | 70.000 | 0.00 | 0.00 |
| 7.18 | 0.615 | 7.18 | 69.385 | 171 | 2.43 |
| 14.37 | 2.461 | 14.37 | 67.539 | 342 | 2.43 |
| 21.55 | 5.536 | 21.55 | 64.464 | 514 | 2.43 |
| 28.74 | 9.842 | 28.74 | 60.158 | 685 | 2.43 |
| 35.92 | 15.379 | 35.92 | 54.621 | 856 | 2.43 |
| 43.11 | 22.146 | 43.11 | 47.854 | 1027 | 2.43 |
| 50.29 | 30.143 | 50.29 | 39.857 | 1199 | 2.43 |
| 57.48 | 39.370 | 57.48 | 30.630 | 1370 | 2.43 |
| 64.66 | 49.827 | 64.66 | 20.173 | 1541 | 2.43 |
| 71.85 | 61.515 | 71.85 | 8.485 | 1712 | 2.43 |

| Forward Linear Segment | | | | | |
|---|---|---|---|---|---|
| Linear Time | Acceleration Distance | Total Time | Position at Time | Tooth Tip Velocity | Tooth Tip Acceleration |

-continued

High Speed Research Press
Model for Rotary Nip Processes

| (msec) | (mm) | (msec) | (mm) | (mm/sec) | (g's) |
|---|---|---|---|---|---|
| 0.00 | 0.000 | 71.85 | 8.485 | 1712 | 2.43 |
| 0.40 | 0.685 | 72.25 | 7.800 | 1712 | 0.00 |
| 0.80 | 1.370 | 72.65 | 7.115 | 1712 | 0.00 |
| 1.20 | 2.055 | 73.05 | 6.430 | 1712 | 0.00 |
| 1.60 | 2.740 | 73.45 | 5.745 | 1712 | 0.00 |
| 2.00 | 3.425 | 73.85 | 5.060 | 1712 | 0.00 |

Forward Transition Segment

| Transition Time (msec) | Transition Distance (mm) | Total Time (msec) | Position at Time (mm) | Tooth Tip Velocity (mm/sec) | Tooth Tip Acceleration (g's) |
|---|---|---|---|---|---|
| 0.00 | 0.000 | 73.85 | 5.060 | 1712 | 0.00 |
| 0.31 | 0.531 | 74.16 | 4.529 | 1710 | −1.58 |
| 0.62 | 1.060 | 74.47 | 4.000 | 1703 | −3.17 |
| 0.93 | 1.586 | 74.78 | 3.474 | 1691 | −4.75 |
| 1.24 | 2.107 | 75.09 | 2.952 | 1674 | −6.33 |
| 1.55 | 2.623 | 75.40 | 2.437 | 1652 | −7.91 |
| 1.86 | 3.131 | 75.71 | 1.928 | 1626 | −9.50 |
| 2.17 | 3.631 | 76.02 | 1.429 | 1594 | −11.08 |
| 2.48 | 4.119 | 76.33 | 0.940 | 1558 | −12.66 |
| 2.79 | 4.596 | 76.64 | 0.463 | 1517 | −14.24 |
| 3.10 | 5.060 | 76.95 | 0.000 | 1472 | −15.83 |

Engagement Segment

| Engagement Time (msec) | Engagement Distance (mm) | Total Time (msec) | Position at Time (mm) | Tooth Tip Velocity (mm/sec) | Tooth Tip Acceleration (g's) |
|---|---|---|---|---|---|
| 0 | 0.000 | 76.95 | 0.000 | 1472 | −15.83 |
| 0.92 | 1.286 | 77.86 | −1.286 | 1328 | −15.97 |
| 1.84 | 2.441 | 78.78 | −2.441 | 1184 | −16.09 |
| 2.76 | 3.461 | 79.70 | −3.461 | 1038 | −16.20 |
| 3.68 | 4.348 | 80.62 | −4.348 | 892 | −16.30 |
| 4.59 | 5.099 | 81.54 | −5.099 | 744 | −16.38 |
| 5.51 | 5.715 | 82.46 | −5.715 | 596 | −16.45 |
| 6.43 | 6.195 | 83.38 | −6.195 | 448 | −16.50 |
| 7.35 | 6.538 | 84.30 | −6.538 | 299 | −16.54 |
| 8.27 | 6.743 | 85.22 | −6.743 | 149 | −16.56 |
| 9.19 | 6.812 | 86.13 | −6.812 | 0 | −16.57 |

Disengagement Segment

| Engagement Time (msec) | Engagement Distance (mm) | Total Time (msec) | Position at Time (mm) | Tooth Tip Velocity (mm/sec) | Tooth Tip Acceleration (g's) |
|---|---|---|---|---|---|
| 0.00 | 6.812 | 86.13 | −6.812 | 0 | −16.57 |
| 0.92 | 6.743 | 87.05 | −6.743 | −149 | −16.56 |
| 1.84 | 6.538 | 87.97 | −6.538 | −299 | −16.54 |
| 2.76 | 6.195 | 88.89 | −6.195 | −448 | −16.50 |
| 3.68 | 5.715 | 89.81 | −5.715 | −596 | −16.45 |
| 4.59 | 5.099 | 90.73 | −5.099 | −744 | −16.38 |
| 5.51 | 4.348 | 91.65 | −4.348 | −892 | −16.30 |
| 6.43 | 3.461 | 92.57 | −3.461 | −1038 | −16.20 |
| 7.35 | 2.441 | 93.48 | −2.441 | −1184 | −16.09 |
| 8.27 | 1.286 | 94.40 | −1.286 | −1328 | −15.97 |
| 9.19 | 0.000 | 95.32 | 0.000 | −1472 | −15.83 |

Reverse Transition Segment

| Transition Time (msec) | Transition Distance (mm) | Total Time (msec) | Position at Time (mm) | Tooth Tip Velocity (mm/sec) | Tooth Tip Acceleration (g's) |
|---|---|---|---|---|---|
| 0.00 | 0.000 | 95.32 | 0.000 | −1472 | −15.83 |
| 0.31 | 0.531 | 95.63 | 0.531 | −1517 | −14.24 |
| 0.62 | 1.060 | 95.94 | 1.060 | −1558 | −12.66 |
| 0.93 | 1.586 | 96.25 | 1.586 | −1594 | −11.08 |
| 1.24 | 2.107 | 96.56 | 2.107 | −1626 | −9.50 |
| 1.55 | 2.623 | 96.87 | 2.623 | −1652 | −7.91 |
| 1.86 | 3.131 | 97.18 | 3.131 | −1674 | −6.33 |

-continued

High Speed Research Press
Model for Rotary Nip Processes

| 2.17 | 3.631 | 97.49 | 3.631 | −1691 | −4.75 |
| 2.48 | 4.119 | 97.80 | 4.119 | −1703 | −3.17 |
| 2.79 | 4.596 | 98.11 | 4.596 | −1710 | −1.58 |
| 3.10 | 5.060 | 98.42 | 5.060 | −1712 | 0.00 |

Reverse Linear Segment

| Linear Time (msec) | Acceleration Distance (mm) | Total Time (msec) | Position at Time (mm) | Tooth Tip Velocity (mm/sec) | Tooth Tip Acceleration (g's) |
|---|---|---|---|---|---|
| 0.00 | 0.000 | 98.42 | 5.060 | −1712 | 0.00 |
| 0.40 | 0.685 | 98.82 | 5.745 | −1712 | 0.00 |
| 0.80 | 1.370 | 99.22 | 6.430 | −1712 | 0.00 |
| 1.20 | 2.055 | 99.62 | 7.115 | −1712 | 0.00 |
| 1.60 | 2.740 | 100.02 | 7.800 | −1712 | 0.00 |
| 2.00 | 3.425 | 100.42 | 8.485 | −1712 | 2.43 |

Reverse Acceleration Segment

| Acceleration Time (msec) | Acceleration Distance (mm) | Total Time (msec) | Position at Time (mm) | Tooth Tip Velocity (mm/sec) | Tooth Tip Acceleration (g's) |
|---|---|---|---|---|---|
| 0.00 | 0.000 | 100.42 | 8.485 | −1712 | 2.43 |
| 7.18 | 11.688 | 107.61 | 20.173 | −1541 | 2.43 |
| 14.37 | 22.146 | 114.79 | 30.630 | −1370 | 2.43 |
| 21.55 | 31.373 | 121.98 | 39.857 | −1199 | 2.43 |
| 28.74 | 39.370 | 129.16 | 47.854 | −1027 | 2.43 |
| 35.92 | 46.137 | 136.35 | 54.621 | −856 | 2.43 |
| 43.11 | 51.673 | 143.53 | 60.158 | −685 | 2.43 |
| 50.29 | 55.979 | 150.71 | 64.464 | −514 | 2.43 |
| 57.48 | 59.055 | 157.90 | 67.539 | −342 | 2.43 |
| 64.66 | 60.900 | 165.08 | 69.385 | −171 | 2.43 |
| 71.85 | 61.515 | 172.27 | 70.000 | 0 | 0.00 |

What is claimed is:

1. A simulation press comprising:
a fixed main body;
a carriage associated with said main body for movement relative to said main body;
a first plate coupled to said fixed main body and being adapted to engage a workpiece;
a second plate coupled to said carriage for movement with said carriage, said second plate also being adapted to engage said workpiece;
at least one motor apparatus coupled to said fixed main body and said carriage for effecting movement of said carriage relative to said main body;
a drive controller coupled to said at least one motor apparatus for controlling the operation of said at least one motor apparatus in response to feedback from at least one feedback sensor so as to cause said second plate to move relative to said first plate such that said first and second plates engage said workpiece and simulate a ring rolling operation on said workpiece.

2. A simulation press as set forth in claim 1, wherein said at least one motor apparatus comprises at least one servo linear motor.

3. A simulation press as set forth in claim 2, wherein said at least one motor apparatus further comprises at least one amplifier which is coupled to said drive controller and said at least one servo linear motor.

4. A simulation press as set forth in claim 1, wherein said carriage reciprocates linearly relative to said fixed main body.

5. A simulation press as set forth in claim 1, wherein said first plate is coupled to said fixed main body via a coupling structure, said coupling structure including at least one force sensor for sensing a force generated during engagement of said workpiece by said first and second plates, said controller increasing a force generated by said at least one motor apparatus in response to a force sensed by said at least one force sensor, said at least one force sensor comprising said at least one feedback sensor.

6. A simulation press as set forth in claim 5, wherein said at least one force sensor comprises at least one load cell.

7. A simulation press as set forth in claim 6, wherein said at least one feedback sensor further comprising a linear encoder read head coupled to said fixed main body and a sensor strip coupled to said carriage, said read head reading position values from said sensor strip and generating corresponding signals to said controller.

8. A simulation press as set forth in claim 7, wherein predetermined discrete time intervals and corresponding carriage positions are provided to said controller and said controller controlling the operation of said at least one motor apparatus so as to control the movement of said carriage based on the carriage positions provided to the controller and in response to the signals generated by said read head and said at least one load cell.

9. A simulation press as set forth in claim 8, wherein at least a portion of said carriage positions are determined via the following equation:

$$E(t) = E_M - Di \cdot \left[1 - \cos\left[a\cos\left(1 - \frac{E_M}{Di}\right) \cdot \left(\frac{t}{T} - 1\right)\right]\right]$$

wherein $E_M$ is equal to the maximum depth of engagement of first and second teeth on first and second rolls, the operation of which is being simulated;

Di is equal to the diameter of the first and second rolls;

t is equal to the process time and has a value from 0 to 2T; and

T is equal to one-half of the total time a given point on a workpiece is engaged by the first and second teeth on the first and second rolls.

10. A simulation press as set forth in claim 6, wherein said fixed main body comprises:

an outer support member;

a pair of L-shaped limiting members associated with said outer support member;

a spring-loading plate; and a least one adjustment member associated with said outer support member and said spring-loading plate for adjusting the position of said spring-loading plate.

11. A simulation press as set forth in claim 10, wherein said coupling structure comprises:

a spring-loaded plate positioned between said spring-loading plate and said L-shaped limiting members; and at least one compression spring positioned between said spring-loading plate and said spring-loaded plate for biasing said spring-loaded plate against said L-shaped limiting members.

12. A simulation press as set forth in claim 11, wherein said coupling structure further comprises:

a first cooling plate coupled to said spring-loaded plate;

a first heated plate coupled to said first cooling plate; and said first workpiece-engaging plate being coupled to said first heated plate.

13. A simulation press as set forth in claim 12, wherein said at least one load cell is positioned between said first cooling plate and said first heated plate.

14. A simulation press as set forth in claim 1, wherein said carriage comprises:

a carriage main body portion;

a second cooling plate coupled to said carriage main body portion;

a second heated plate coupled to said second cooling plate; and said second workpiece-engaging plate being coupled to said second heated plate.

15. A simulation press as set forth in claim 1, wherein said first workpiece-engaging plate comprises first teeth and said second workpiece-engaging plate comprises second teeth and said controller controls the operation of said at least one motor apparatus such that said second plate is moved relative to said first plate so that said second teeth are moved to a maximum engagement depth relative to said first teeth.

16. A simulation press as set forth in claim 15, wherein said controller controls the operation of said at least one motor apparatus such that movement of tip portions of said second teeth follow a position vs. time curve having a substantially parabolic shape.

17. A simulation press comprising:

a fixed main body;

a carriage associated with said main body for linear movement relative to said main body;

a first plate coupled to said fixed main body and being adapted to engage a workpiece;

a second plate coupled to said carriage for movement with said carriage, said second plate also being adapted to engage said workpiece;

at least one linear servo motor apparatus coupled to said fixed main body and said carriage for effecting movement of said carriage relative to said main body; and a drive controller coupled to said at least one servo linear motor apparatus for controlling the operation of said at least one motor apparatus so as to effect reciprocating linear movement of said carriage thereby causing said second plate to move relative to said first plate such that said first and second plates engage said workpiece and simulate a ring rolling operation on said workpiece.

18. A simulation press as set forth in claim 17, wherein said at least one servo linear motor apparatus further comprises at least one amplifier which is coupled to said drive controller and said at least one servo linear motor.

19. A method of simulating a ring rolling operation on a workpiece comprising the steps of:

providing a first plate having first teeth;

providing a second plate having second teeth; and moving said second plate relative to said first plate in accordance with a position vs. time curve having a generally parabolic shape such that said first and second plates engage a workpiece and simulate a ring rolling operation on said workpiece.

20. A method of simulating a ring rolling operation on a workpiece as set forth in claim 19 further comprising the step of determining strain and a strain rate experienced by the workpiece during engagement by said first and second plates.

* * * * *